(12) United States Patent
Izquierdo Torres et al.

(10) Patent No.: US 10,660,848 B2
(45) Date of Patent: May 26, 2020

(54) OPHTHALMIC COMPOSITIONS

(71) Applicant: Laboratorios Salvat, S.A., Esplugues de LLobregat-Barcelona (ES)

(72) Inventors: Francisca Izquierdo Torres, Esplugues de LLobregat-Barcelona (ES); Sandra Marchan Sancho, Esplugues de LLobregat-Barcelona (ES); Isabel Delgado Gañán, Esplugues de LLobregat-Barcelona (ES)

(73) Assignee: LABORATORIOS SALVAT, S.A., Barcelona (ES)

( * ) Notice: Subject to any disclaimer, the term of this patent is extended or adjusted under 35 U.S.C. 154(b) by 0 days.

(21) Appl. No.: 15/644,286

(22) Filed: Jul. 7, 2017

(65) Prior Publication Data
US 2018/0008538 A1 Jan. 11, 2018

(30) Foreign Application Priority Data

Jul. 7, 2016 (EP) .................................... 16382321

(51) Int. Cl.
| | |
|---|---|
| *A61K 9/00* | (2006.01) |
| *A61K 9/107* | (2006.01) |
| *A61K 31/18* | (2006.01) |
| *A61K 31/4166* | (2006.01) |
| *A61K 36/45* | (2006.01) |
| *A61K 47/14* | (2017.01) |
| *A61K 47/44* | (2017.01) |

(52) U.S. Cl.
CPC .......... *A61K 9/0048* (2013.01); *A61K 9/1075* (2013.01); *A61K 31/18* (2013.01); *A61K 31/4166* (2013.01); *A61K 36/45* (2013.01); *A61K 47/14* (2013.01); *A61K 47/44* (2013.01)

(58) Field of Classification Search
CPC .... A61K 9/0048; A61K 9/1075; A61K 31/18; A61K 31/4166; A61K 36/45; A61K 47/14; A61K 47/44
See application file for complete search history.

(56) References Cited

U.S. PATENT DOCUMENTS

| | | | |
|---|---|---|---|
| 5,981,607 A | 11/1999 | Ding et al. | |
| 8,372,434 B2* | 2/2013 | Bague ................. | A61K 9/0048 424/489 |
| 2010/0286121 A1* | 11/2010 | Rohrs ................. | A61K 9/0019 514/211.15 |
| 2013/0108674 A1* | 5/2013 | Mangiafico ........... | A61K 9/0048 424/400 |
| 2014/0275263 A1* | 9/2014 | Wassel ............... | A61K 9/1075 514/569 |

FOREIGN PATENT DOCUMENTS

| | | | |
|---|---|---|---|
| CN | 1686533 A | * | 10/2005 |
| CN | 101028240 A | * | 9/2007 |
| CN | 105726479 A | * | 7/2016 |
| DE | 3102593 | | 9/1982 |
| EP | 2659903 | | 11/2013 |
| WO | WO-2004098592 | | 11/2004 |
| WO | WO-2009061607 | | 5/2009 |
| WO | WO-2010141648 | | 12/2010 |
| WO | WO-2013086438 | | 6/2013 |
| WO | WO-2013086449 | | 6/2013 |
| WO | WO-2014153733 | | 10/2014 |
| WO | WO-2014160079 | | 10/2014 |

OTHER PUBLICATIONS

Zhang Jing, Liu Zhi-hong, Wang Hui-juan, Liu Jian-qing, and Song Hong-tao, "Preparation of cyclosporin A submicron emulsion for ocular administration", Chinese Journal of Hospital Pharmacy, 2014, 34(18), 1558-1562. (Year: 2014).*

Lin Ying, Kohei Tahara, Hirofumi Takeuchi, "Drug delivery to the ocular posterior segment using lipid emulsion via eye drop administration: Effect of emulsion formulations and surface modification", International Journal of Pharmaceutics 453 (2013) 329-335. (Year: 2013).*

Smadar Cohen, Esther Lobel, Amira Trevgoda, Yael Peled, "A novel in situ-forming ophthalmic drug delivery system from alginates undergoing gelation in the eye", Journal of Controlled Release 44 (1997) 201-208. (Year: 1997).*

Muhannad Jumaa and Bernd W. Muller, "The effect of oil components and homogenization conditions on the physicochemical properties and stability of parenteral fat emulsions", International Journal of Pharmaceutics, 163 (1998), 81-89. (Year: 1998).*

Shunmugaperumal Tamilvanan and Simon Benita, "The potential of lipid emulsion for ocular delivery of lipophilic drugs", European Journal of Pharmaceutics and Biopharmaceutics, 58 (2004), 357-368. (Year: 2004).*

Alba, Rodolfo M., et al., "The Effect on the Cornea of Various Vehicles for Cyclosporin Eye Drops", Folia Ophthalmol. Jpn. 40: 902-908, 1989, (1989), 902-908.

Albietz, Julie, et al., "Management of Filamentary Keratitis Associated with Aqueous-Deficient Dry Eye", Optometry and Vision Science, vol. 80, No. 6, pp. 420-430, (Jun. 2003), 420-430.

Arakaki, Rieko, et al., "Anti-Inflammatory Effects of Rebamipide Eyedrop Administration on Ocular Lesions in a Murine Model of Primary Sjogren's Syndrome", PLOS ONE, May 2014, vol. 9, Issue 5, e98390, (May 2014), 7 pgs.

(Continued)

*Primary Examiner* — Mina Haghighatian
*Assistant Examiner* — Nathan W Schlientz
(74) *Attorney, Agent, or Firm* — Hultquist, PLLC; Steven J. Hultquist

(57) ABSTRACT

The present invention relates to a sterile ophthalmic composition comprising castor oil and a medium chain triglyceride, to its use in medicine, in particular for the treatment and/or prevention of an ocular disease selected from the group consisting of dry eye, conjunctivitis, dermatitis, blepharitis, entropion, floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis, episcleritis and uveitis.

12 Claims, 5 Drawing Sheets
Specification includes a Sequence Listing.

(56) References Cited

OTHER PUBLICATIONS

Barabino, Stefano, et al., "The Effect of Preservatives and Antiglaucoma Treatments on the Ocular Surface of Mice With Dry Eye", Invest Ophthalmol Vis Sci. 2014;55:6499-6504, (Aug. 31, 2014), 6499-6504.

Baudouin, Christophe, et al., "Preservatives in eyedrops: The good, the bad and the ugly", Progress in Retinal and Eye Research 29 (2010) 312-334, (2010), 312-334.

Chen, Ying-Ting, et al., "Corneal Epithelial Damage During Lasik: A Review of 1873 Eyes", Journal of Refractive Surgery, vol. 23, Nov. 2007, 916-923, (Jul. 31, 2007), 916-923.

Colligris, Basilio, "An update on dry eye disease molecular treatment: advances in drug pipelines", Expert Opin. Pharmacother. (2014) 15(10):1371-1390, (2014), 1371-1390.

Corrales, Rosa M., et al., "Ocular Mucin Gene Expression Levels as Biomarkers for the Diagnosis of Dry Eye Syndrome", Invest Ophthalmol Vis Sci. 2011;52(11):8363-8369, (Oct. 2011), 8363-8369.

Dausch, D., et al., "Comparative Study of Treatment of the Dry Eye Syndrome due to Disturbances of the Tear Film Lipid Layer with Lipid-Containing Tear Substitutes: Efficacy of lipid-containing tear substitutes", Klin Monatsbl Augenheilkd 2006; 223: 974-983, (May 8, 2006), 974-983.

Di Pascuale, Mario A., et al., "Sequential Changes of Lipid Tear Film after the Instillation of a Single Drop of a New Emulsion Eye Drop in Dry Eye Patients", Ophthalmology 2004;111(4):783-791, (Apr. 2004), 783-791.

Dogru, Murat, et al., "Ocular Surface and MUC5AC Alterations in Atopic Patients with Corneal Shield Ulcers", Current Eye Research, 30:897-908, 2005, (Mar. 5, 2005), 897-908.

Dorennavar, Laxmi, et al., "The role of Rebamipide ophthalmic suspension in management of dry eye disease", Indian Journal of Clinical and Experimental Ophthalmology, Oct.-Dec. 2015;1(4):191-196, (Dec. 2015), 191-196.

Goto, Eiki, et al., "Low-concentration Homogenized Castor Oil Eye Drops for Noninamed Obstructive Meibomian Gland Dysfunction", Ophthalmology, vol. 109, No. 11, Nov. 2002:2030-2035, (Nov. 2002), 2030-2035.

Han, Kyung Eun, et al., "Epithelial Wound Healing After Cataract Surgery Comparing Two Different Topical Fluoroquinolones", Yonsei Med J., vol. 55, No. 1, Jan. 2014; 197-202, (Jan. 2014), 197-202.

Hasegawa, Takashi, et al., "Corneal-Protective Effects of an Artificial Tear Containing Sodium Hyaluronate and Castor Oil on a Porcine Short-Term Dry Eye Model", J Vet Med Sci 76(9): 1219-1224, 2014, (May 30, 2014), 1219-1224.

Kaercher, Thomas, et al., "A prospective, multicenter, noninterventional study of Optive Plus® in the treatment of patients with dry eye: the prolipid study", Clinical Ophthalmology 2014:8 1147-1155, (Jun. 2014), 1147-1155.

Kardon, Rachele, et al., "Bacterial Conjunctivitis in Muc1 Null Mice", Investigative Ophthalmology & Visual Science, Jun. 1999, vol. 40, No. 7, 1328-1335, (Jun. 1999), 1328-1335.

Khanal, Santosh, et al., "Effect of an Oil-in-Water Emulsion on the Tear Physiology of Patients With Mild to Moderate Dry Eye", Cornea 2007;26(2):175-181, (Feb. 2007), 175-181.

Lee, Jang Hoon, et al., "Effectiveness and Optical Quality of Topical 3.0% Diquafosol versus 0.05% Cyclosporine A in Dry Eye Patients following Cataract Surgery", Journal of Ophthalmology, vol. 2016, Article ID 8150757, 7 pages, (Jan. 21, 2016), 7 pgs.

Lee, Sze-Yee, et al., "Lipid-Containing Lubricants for Dry Eye: A Systematic Review", Optometry and Vision Science, vol. 89, No. 11, Nov. 2012; 1654-1661, (Nov. 2012), 1654-1661.

Liu, Xing, et al., "Therapeutic Effects of Sodium Hyaluronate on Ocular Surface Damage Induced by Benzalkonium Chloride Preserved Anti-glaucoma Medications", Chin Med J 2015;128(18):2444-9, (Apr. 25, 2015), 2444-2449.

Maissa, Cecile, et al., "Effect of castor oil emulsion eyedrops on tear film composition and stability", Contact Lens & Anterior Eye 33 (2010) 76-82, (2010), 76-82.

Mantelli, Flavio, et al., "Functions of ocular surface mucins in health and disease", Curr Opin Allergy Clin Immunol. Oct. 2008; 8(5): 477-483, (Oct. 2008), 477-483.

Mastromarino, A., et al., "The Effect of Medium Chain Triglycerides-Containing Tear Substitute on the Dynamics of Lipid Layer Interference Patterns (DLIP) in Dry Eye Patients", Investigative Ophthalmology & Visual Science May 2005, vol. 46, 2043, (May 2005), 2 pgs.

Mimura, Tatsuya, et al., "Relation Between Total Tear IgE and Severity of Acute Seasonal Allergic Conjunctivitis", Current Eye Research, 37(10), 864-870, 2012, (Apr. 23, 2012), 864-870.

Miyoshi, Takahiro, et al., "Interleukin-8 Concentrations in Conjunctival Epithelium Brush Cytology Samples Correlate With Neutrophil, Eosinophil Infiltration, and Corneal Damage", Cornea 20(7): 743-747, 2001, (Apr. 3, 2001), 743-747.

Mohan, Kale, et al., "Ophthalmic Microemulsion: A Comprehensive Review", Int J Pharm Bio Sci Jul. 2012; 3(3):1-13, (Jul. 2012), 1-13.

Mori, Yosai, et al., "Effect of Diquafosol Tetrasodium Eye Drop for Persistent Dry Eye After Laser In Situ Keratomileusis", Cornea, vol. 33, No. 7, Jul. 2014; 659-662, (Jul. 2014), 659-662.

Nejima, Ryohei, et al., "Corneal Barrier Function, Tear Film Stability, and Corneal Sensation After Photorefractive Keratectomy and Laser In Situ Keratomileusis", American Journal of Ophthalmology, Corneal Barrier and Tear Stability After PRK and Lasik, vol. 139, No. 1, Jan. 2005; 64-71, (Jan. 2005), 64-71.

O'Brien, Terrence P., et al., "Efficacy of Ofloxacin vs Cefazolin and Tobramycin in the Therapy for Bacterial Keratitis", Arch Ophthalmol. 1995;113:1257-1265, (1995), 1257-1265.

Oh, Taehoon, et al., "Changes in the tear film and ocular surface after cataract surgery", Jpn J Ophthalmol (2012) 56:113-118, (Feb. 3, 2012), 113-118.

Salman, Ilknur Akyol, et al., "Epithelial healing in experimental corneal alkali wounds with nondiluted autologous serum eye drops", Cutaneous and Ocular Toxicology, 2010; 29(2): 116-121, (Feb. 13, 2010), 116-121.

Scardovi, C., et al., "Epidermal Growth Factor in the Topical Treatment of Traumatic Corneal Ulcers", Ophthalmologica 1993; 206:119-124, (1993), 119-124.

Sehic, Amer, et al., "Pre-Clinical Cell-Based Therapy for Limbal Stem Cell Deficiency", J. Funct. Biomater. 2015, 6, 863-888, (Aug. 28, 2015), 863-888.

Simmons, Peter A., et al., "Efficacy, Safety, and Acceptability of a Lipid-Based Artificial Tear Formulation: A Randomized, Controlled, Multicenter Clinical Trial", Clinical Therapeutics, vol. 37, No. 4, 2015; 858-868, (Apr. 2015), 858-868.

Tchedre, Kissaou T., et al., "Assessment of Effects of Multipurpose Contact Lens Care Solutions on Human Corneal Epithelial Cells", Letter to the Editor: Eye & Contact Lens, vol. 37, No. 5, Sep. 2011; 328-330, (Sep. 2011), 328-330.

Toda, Ikuko, et al., "Combination Therapy With Diquafosol Tetrasodium and Sodium Hyaluronate in Patients With Dry Eye After Laser In Situ Keratomileusis", American Journal of Ophthalmology, Effect of Diquafosol and Hyaluronate in Dry Eye After Lasik, 157(3); 616-622, (Mar. 2014), 616-622.

Tsai, Ray Jui-Fang, et al., "Reconstruction of Damaged Corneas by Transplantation of Autologous Limbal Epithelial Cells", The New England Journal of Medicine, vol. 343, No. 2, Jul. 13, 2000, 86-93, (Jul. 13, 2000), 86-93.

Uchino, Yuichi, et al., "Alteration of Tear Mucin 5AC in Office Workers Using Visual Display Terminals: The Osaka Study", JAMA Ophthalmol. 2014;132(8):985-992, (Jun. 5, 2014), 985-992.

Versura, Piera, et al., "Efficacy of Standardized and Quality-Controlled Cord Blood Serum Eye Drop Therapy in the Healing of Severe Corneal Epithelial Damage in Dry Eye", Cornea, vol. 32, No. 4, Apr. 2013, 412-418, (Apr. 2013), 412-418.

Wan, Pengxia, et al., "Cell Delivery with Fixed Amniotic Membrane Reconstructs Corneal Epithelium in Rabbits with Limbal Stem Cell Deficiency", Investigative Ophthalmology & Visual Science, Feb. 2011, vol. 52, No. 2, 724-730, (Feb. 2011), 724-730.

(56) References Cited

OTHER PUBLICATIONS

Wipperman, Jennifer L., et al., "Evaluation and Management of Corneal Abrasions", Am Fam Physician, vol. 87, No. 2, Jan. 15, 2013, 114-120, (Jan. 15, 2013), 114-120.

Zhang, Wenjian, et al., "A novel nanoscale-dispersed eye ointment for the treatment of dry eye disease", Nanotechnology 25 (2014) 125101, (Feb. 26, 2014), 10 pgs.

\* cited by examiner

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: A synthetic primer MUC5AC F

<400> SEQUENCE: 1
cccacagaac ccagtacaa                                                19

<210> SEQ ID NO 2
<211> LENGTH: 18
<212> TYPE: DNA
<213> ORGANISM: Artificial Sequence
<220> FEATURE:
<223> OTHER INFORMATION: A synthetic primer MUC5AC R

<400> SEQUENCE: 2
aatgtgtagc cctcgtct                                                 18

<210> SEQ ID NO 3
<211> LENGTH: 20
<212> TYPE: DNA
<213> ORGANISM: Artificial Sequence
<220> FEATURE:
<223> OTHER INFORMATION: A synthetic primer MUC1 F

<400> SEQUENCE: 3
aggctcagct tctactctgg                                               20

<210> SEQ ID NO 4
<211> LENGTH: 20
<212> TYPE: DNA
<213> ORGANISM: Artificial Sequence
```

```
<220> FEATURE:
<223> OTHER INFORMATION: A synthetic primer MUC1 R

<400> SEQUENCE: 4
gacagacagc caaggcaatg                                           20

<210> SEQ ID NO 5
<211> LENGTH: 20
<212> TYPE: DNA
<213> ORGANISM: Artificial Sequence
<220> FEATURE:
<223> OTHER INFORMATION: A synthetic primer beta-actin F

<400> SEQUENCE: 5
gacatcaagg agaagctgtg                                           20

<210> SEQ ID NO 6
<211> LENGTH: 20
<212> TYPE: DNA
<213> ORGANISM: Artificial Sequence
<220> FEATURE:
<223> OTHER INFORMATION: A synthetic primer beta-actin R

<400> SEQUENCE: 6
agctcgtagc tcttctccag                                           20
```

OPHTHALMIC COMPOSITIONS

CLAIM OF PRIORITY

This application claims the benefit of priority of European Patent Application No. EP16382321.4, filed on Jul. 7, 2016, the benefit of priority of which is claimed hereby, and which is incorporated by reference herein in its entirety.

FIELD OF THE INVENTION

The present invention relates to ophthalmic compositions comprising a mixture of castor oil and medium chain triglyceride and their use in the treatment of ocular diseases.

BACKGROUND OF THE INVENTION

The cornea is the transparent front part of the eye that covers the iris, pupil, and anterior chamber. The human cornea has several layers. The outermost layer is the corneal epithelium, an exceedingly thin multicellular epithelial tissue layer (non-keratinized stratified squamous epithelium) of fast-growing and easily regenerated cells, kept moist with tears. Irregularity or edema of the corneal epithelium disrupts the smoothness of the air/tear-film interface, the most significant component of the total refractive power of the eye, thereby reducing visual acuity. It is continuous with the conjunctival epithelium, and is composed of several layers of cells which are shed constantly on the exposed layer and are regenerated by multiplication in the basal layer.

The conjunctiva lines the inside of the eyelids and covers the sclera. It is composed of non-keratinized, stratified columnar epithelium with goblet cells, and also stratified columnar epithelium. The conjunctiva helps lubricate the eye by producing mucus and tears, although a smaller volume of tears than the lacrimal gland. It also contributes to immune surveillance and helps to prevent the entrance of microbes into the eye.

The tear film coating the eye, known as the precorneal film, has three distinct layers, from the most outer surface: lipid layer, aqueous layer and mucous layer. The mucus layer coats the cornea, provides a hydrophilic layer and allows for even distribution of the tear film. The mucins present in the tear film serve to maintain the hydration of the ocular surface and to provide lubrication and anti-adhesive properties between the cells of the ocular surface and conjunctiva during the blink and to contribute to the epithelial barrier to prevent pathogens from binding to the ocular surface.

Disorders of the conjunctiva and cornea are a common source of eye complaints since the surface of the eye is exposed to various external influences and is especially susceptible to trauma, infections, chemical irritation, allergic reactions and dryness.

Re-epithelization of the conjunctiva and/or cornea and/or increase in mucin production, in particular MUC1 and MUC5AC, are strategies for the management of several ocular diseases, such as dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis.

Dry eye is a common disorder provoking changes in tear film and ocular surface. Dry eye occurs when the eye does not produce tears properly, or when the tears are not of the correct consistency and evaporate too quickly. Untreated dry eye can cause ocular infections, corneal ulcer and blindness [Colligris et al., *Exper Opin Pharmacother.* 2014, 15, 1371-1390]. The term dry eye is used in the present invention to encompass keratoconjunctivitis sicca, xerophthalmia, xerosis and Sjögren's syndrome. A therapeutic approach for the treatment of dry eye is healing of the injured corneal epithelium [Versura et al., *Cornea.* 2013, 32, 412-418]. Moreover, ocular mucin expression levels, in particular MUC1, MUC2, MUC4 and MUC5AC, have been reported to be significantly lower in patients with dry eye syndrome [Corrales et al., *Invest Ophthalmol Vis Sci.* 2011, 52, 8363-8369; Uchino et al., *JAMA Ophthalmol.* 2014, 132, 985-992]. Thus, promoting mucin production, in particular MUC5AC, is also a promising therapeutic approach for managing dry eye. Examples of this treatment route is described in Toda et al., *Amer. J. Ophthalmology.* 2014, 157, 616-622 and Arakaki et al., *PLOS One,* 2014, 9(5), e98390 (1-7). Moreover, lubrication of the surface of the eye and helping tears to remain on the surface of the eye improves the symptoms of dry eye. Thus, artificial tear formulations, such as lipid-based artificial tear formulations comprising either castor oil or a medium chain triglyceride, have been disclosed for the treatment of dry eye disease [Simmons et al., *Clinical Therapeutics.* 2015, 37, 858-868; Hasegawa et al., *J Vet Med Sci.,* 2014, 76, 1219-1224; Kaercher et al., *Clinical Ophthalmology.* 2014, 8, 1147-1155; Zhang et al., *Nanothecnology.* 2014, 25, 125101; Maïssa et al., *Contact Lens Anterior Eye.* 2010, 33, 76-82; Khanal et al., *Cornea.* 2007, 26, 175-181; Mohan et al., *Int J Pharm Bio Sci.* 2012, 3, 1-13; WO 2014/153733 A1; WO 2013/086449 A1; WO 2013/086438 A1; WO 2010/141648 A2].

Conjunctivitis is a common condition that causes redness and inflammation of the conjunctiva. The term conjunctivitis is used in the present invention to encompass allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis. Allergic conjunctivitis (which is caused by an allergic reaction to a substance such as pollen or dust mites) and vernal keratoconjuctivitis (allergic eye disease that especially affects young boys) may produce corneal lesions [Mimura et al., *Curr Eye Res.* 2012, 37, 864-870; Miyoshi et al., *Cornea.* 2001, 20, 743-747]. Atopic keratoconjuctivitis (which is a chronic allergic ocular disease that occurs most often in patients with a history of atopic dermatitis) is characterized by alterations of mucin expression, in particular MUC16 and MUC5AC. Mantelli et al., *Curr Opin Allergy Clin Immuniol.* 2008, 8(5), 477-483 reports that in patients with vernal keratoconjuctivitis successful treatment with anti-allergic and anti-inflammatory drugs was associated with increased MUC5AC expression which was decreased in patient suffering from the disease.

Kardon et. al. *Investigative Ophthalmology & Visual Science,* 1999, 40(7), 1328-1335 reports that loss of MUC1 functional protein via homologous recombination leads to an increase in the frequency and severity of conjunctivitis and blepharitis in mice. Thus, re-epithelization and promoting mucin expression, in particular MUC5AC, are key factors in the treatment of these diseases. At present, common treatments of conjunctivitis include ophthalmic compositions comprising antibiotics, antihistamines or steroids.

Benzalkonium chloride (BAK), the preservative most frequently used in eyedrops, has demonstrated its toxic effect in laboratory, experimental and clinical studies. It has been shown to cause disruption of the corneal epithelium barrier [Baudouin et al., *Prog Retin Eye Res.* 2010, 29m 312-334; Barabino et al., *Invest Ophthalmol Vis Sci.* 2014, 55, 6499-6504; Liu et al., *Chin Med J.,* 2015, 128, 2444-2449]. Dorennavar et al., *Indian J. Clin. and Exper. Ophthalmology,* 2015; 1(4):191-196 discloses that rebapamide, a drug which increases mucin production mediated by MUC1 and MUC4 gene expression, is useful in the treatment of dry eye syndrome (caused among others by preservatives present in tear substitutes like benzalkonium chloride, sodium perborate sodium chloride), ocular surface disorders and allergic conjunctivitis. Moreover, goblet cells, which produce MUC5AC, are reduced by treatment with BAK [Barabino et al., Invest Ophthalmol Vis Sci. 2014, 55, 6499-6504]. MUC5AC is a gel-forming secretory mucin. Secretion typically occurs in response to a stimulus, such as a foreign body on the ocular surface. Thus, promoting re-epithelization and mucin production is a promising strategy for managing the damage induced by preservatives.

Ocular surgery, such as photorefractive keratectomy and laser in situ keratomileusis, produces corneal epithelial damage since it compromises corneal barrier function, tear film stability and corneal sensation [Nejima et al., *Am J Ophthalmol.* 2005, 139, 64-71; Chen et al. *J Refract Surg.* 2007, 23, 916-923]. Cataract surgery does also damage the ocular surface and decreases goblet cell density [Oh et al., *Jpn J Ophthalmol.* 2012, 56, 113-118; Ke et al., *Yonsei Med J.* 20014, 55, 197-202]. Lee et al. *J. Ophthalmol.* 2016, 2016, ID 8150757 shows that stimulation of mucin secretion using Diquafosol is a successful strategy to treat dry eye after cataract surgery. Similarly, Mori et al. *Cornea,* 2014, 33(7), 659-662 described that diquafosol treatment increases mucin production and improves the subjective and objective symptoms of persistent dry eye after LASIK. Thus, promoting corneal re-epithelization and mucin production, in particular MUC5AC, allows managing epithelial or anterior chamber damage induced by ocular surgical procedures.

Limbal cell deficiency is characterized by a loss or deficiency of the cells in the limbus that are vital for re-population of the corneal epithelium and to the barrier function of the limbus. When these cells are lost, the corneal epithelium is unable to repair and renew itself. This results in epithelial breakdown and persistent epithelial defects, corneal conjunctivalization and neovascularization, corneal scarring, and chronic inflammation. All of these contribute to loss of corneal clarity, potential vision loss, chronic pain, photophobia, and keratoplasty failure. Optimization of ocular surface health is the first step in the management of limbal cell deficiency. Often, there are constant insults to the corneal epithelium from multiple concurrent external disorders such as dry eyes, ocular surface inflammation, soft contact lens, and drug toxicity from multiple eye medications. Improving ocular surface health provides a better environment for the remaining limbal cells to survive. Promoting corneal re-epithelization is thus useful for the managing limbal cell deficiency [Wan et al., *Invest Ophtalmol Vis Sci.* 2011, 52, 724-730; Tsai et al., *N Engl J Med.* 2000, 343, 86-93; Sehic et al., *J Funct Biomater.* 2015, 6, 863-888]. At present, this is achieved by administration of preservative-free artificial tears, punctual occlusion, topical cyclosporine, preservative free topical cortical steroids or surgery.

Traumatic corneal ulcers, such as those induced by physical agents, contact lenses or chemical agents, are healed by corneal re-epithelization [Scardovi et al., *Ophthalmologica.* 1993, 206, 119-124; Salman et al., *Cutan Ocul Toxicol.* 2010, 29, 116-121; Wipperman et al., *Am Fam Physician.* 2013, 87, 114-120]. It has also been disclosed that MUC5AC expression is significantly lower in eyes with corneal ulcers [Dogru et al., *Curr Eye Res.* 2005, 30, 897-908]. Moreover, goblet cells, which produce MUC5AC, are lost in alkali burns. Thus, promoting corneal re-epithelization and mucin production, in particular MUC5AC, is useful for the treatment of corneal ulcers, such as those induced by physical or chemical agents. At present, corneal ulcer treatment typically involves the use of topical antibiotics or even surgery.

Keratitis is an inflammation of the cornea which may be caused by an infection involving bacteria, viruses, fungi or parasites, or by a minor injury produced, for example, by wearing contact lenses too long. The term keratitis is used in the present invention to encompass Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy. O'Brien et. al., *Arch Ophthalmol.* 1995; 113, 1257-1265 describes that re-epithelization is a relevant end point in evaluating the healing of ulcerous keratitis. Albietz et. al., *Optom Vis Sci.* 2003, 80, 420-430 informs that patients suffering from filamentary keratitis show a reduced goblet cell density and that filamentary keratitis is a condition associated with aqueous-deficient dry eye (keratoconjunctivitis sicca). Thus, promoting corneal re-epithelization and/or mucin production, in particular MUC5AC, allows managing keratitis. At present, keratitis is treated antibacterial, antifungal, or antiviral therapy, steroid drops or wetting drops.

Uveitis is the inflammation of the uvea, the pigmented layer that lies between the inner retina and the outer fibrous layer composed of the sclera and cornea. Thus, promoting corneal re-epithelization and/or mucin production, in particular MUC5AC, allows managing keratitis. Uveitis is typically treated with glucocorticoid steroids.

Dermatitis is inflammation of the skin. Examples of dermatitis are contact dermatitis and atopic dermatitis.

Blepharitis is an eye condition characterized by chronic inflammation of the eyelid. Examples of blepharitis are chronic anterior blepharitis and chronic posterior blepharitis. Kardon et. al. *Investigative Ophthalmology & Visual Science,* 1999, 40(7), 1328-1335 reports that loss of MUC1 functional protein via homologous recombination leads to an increase in the frequency and severity of conjunctivitis and blepharitis in mice. Thus, increasing the expression of MUC1 appears to be a valuable strategy in the treatment of blepharitis.

Entropion is a medical condition in which the eyelid (usually the lower lid) folds inward. It is very uncomfortable, as the eyelashes constantly rub against the cornea and irritate it. Examples of entropion are paralytic entropion and involutional entropion.

Floppy eyelid syndrome is a disease whose most prominent features often include floppy upper eyelids that can be easily everted, as well as papillary conjunctivitis.

Thyroid ophthalmopathy, also known as Graves' ophthalmopathy, is an autoimmune inflammatory disorder affecting the orbit around the eye, characterized by upper eyelid retraction, lid lag, swelling (edema), redness (erythema), conjunctivitis, and bulging eyes (proptosis).

There is a need in the art for alternative treatments for managing ocular diseases, in which re-epithelization and/or mucin production, in particular MUC1 and MUC5AC, are involved, such as dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis, more particularly in the treatment and/or prevention of dry eye, blepharitis, keratitis such as filamentary keratitis and ulcerous keratitis, conjunctivitis including atopic keratoconjunctivitis, epithelial damage induced by preservatives, epithelial or anterior chamber damage induced by ocular surgery, limbal cell deficiency, corneal ulcers induced by physical or chemical agents.

SUMMARY OF THE INVENTION

Surprisingly, the inventors have found that a mixture of castor oil and medium chain triglyceride promotes mucin expression, in particular MUC1 and MUC5AC, and re-epithelization. More surprisingly, the mixture of castor oil and medium chain triglyceride provides a synergistic effect in mucin MUC1 and MUC5AC expression and re-ephithelization, in particular in corneal wounds.

Thus, in a first aspect, the present invention relates to a sterile ophthalmic composition comprising a) an oily phase comprising castor oil and a medium chain triglyceride, b) one or more surfactants and c) an aqueous phase wherein the composition has a pH from 5.0 to 9.0.

In a second aspect, the present invention relates to a sterile ophthalmic composition as defined in the first aspect for use in medicine.

In a third aspect, the present invention relates to a sterile ophthalmic composition as defined in the first aspect for use in the treatment and/or prevention of an ocular disease selected from the group consisting of dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis, more particularly in the treatment and/or prevention of dry eye, blepharitis, keratitis such as filamentary keratitis and ulcerous keratitis, conjunctivitis including atopic keratoconjunctivitis, epithelial damage induced by preservatives, epithelial or anterior chamber damage induced by ocular surgery, limbal cell deficiency, corneal ulcers induced by physical or chemical agents.

In a forth aspect, the present invention relates to the use of a sterile ophthalmic composition as defined in the first aspect for the manufacture of a medicament for the treatment and/or prevention of an ocular disease selected from the group consisting of dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis, more particularly in the treatment and/or prevention of dry eye, blepharitis, keratitis such as filamentary keratitis and ulcerous keratitis, conjunctivitis including atopic keratoconjunctivitis, epithelial damage induced by preservatives, epithelial or anterior chamber damage induced by ocular surgery, limbal cell deficiency, corneal ulcers induced by physical or chemical agents.

In a fifth aspect, the present invention relates to a method for the prevention and/or treatment of an ocular disease selected from the group consisting of dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis, more particularly in the treatment and/or prevention of dry eye, blepharitis, keratitis such as filamentary keratitis and ulcerous keratitis, conjunctivitis including atopic keratoconjunctivitis, epithelial damage induced by preservatives, epithelial or anterior chamber damage induced by ocular surgery, limbal cell deficiency, corneal ulcers induced by physical or chemical agents by administering to a subject in need thereof an effective amount of a sterile ophthalmic composition as defined in the first aspect.

DETAILED DESCRIPTION OF THE INVENTION

Compositions of the Invention

Figure 1:
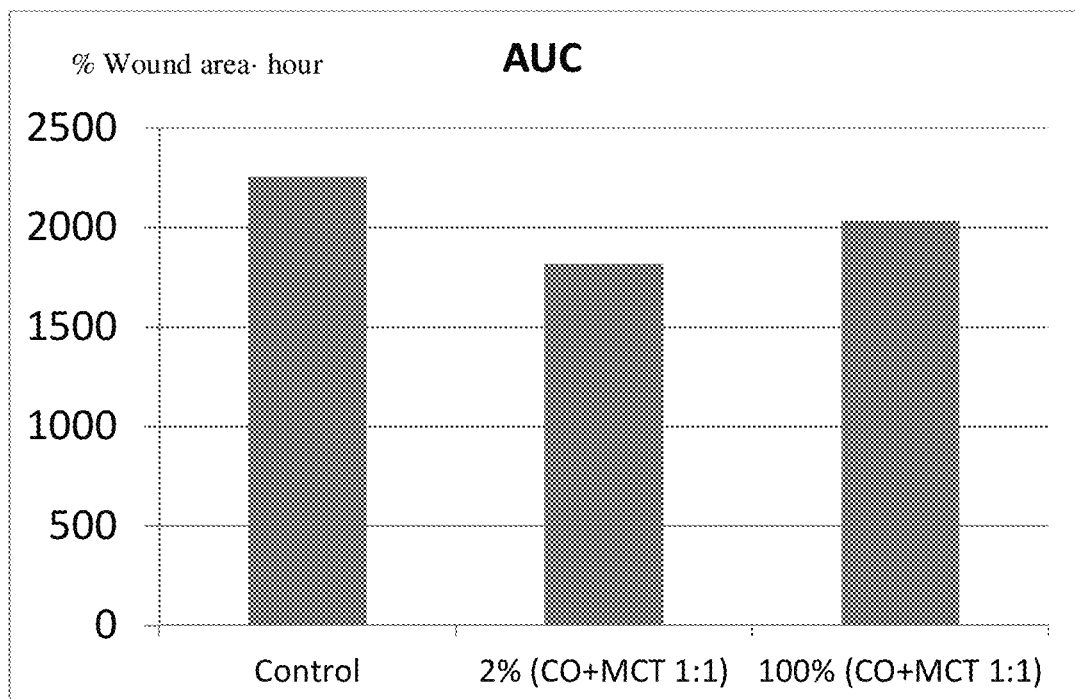
FIG. 1 shows the results obtained in Example 3 relative to the in vivo wound healing promoting effect (expressed as AUC) of mixtures of castor oil and caprylic/capric triglyceride (ratio 1:1) at 2% and 100% concentrations when compared with saline solution (control).

In a first aspect, the present invention relates to a sterile ophthalmic composition comprising a) an oily phase comprising castor oil and a medium chain triglyceride, b) one or more surfactants and c) an aqueous phase, wherein the composition has a pH of 5.0 to 9.0.

In a preferred embodiment the compositions of the present invention do not comprise any one of the following active ingredients:
1. Mesopram (5-(4-Methoxy-3-propoxyphenyl)-5-methyl-1,3-oxazolidin-2-one),
2. Sotalol ((RS)—N-{4-[1-hydroxy-2-(propan-2-ylamino)ethyl]phenyl}methane-sulfonamide); and
3. Cyclosporine A ((3S,6S,9S,12R,15S,18S,21S,24S,30S, 33S)-30-Ethyl-33-[(1R,2R,4E)-1-hydroxy-2-methyl-4-hexen-1-yl]-6,9,18,24-tetraisobutyl-3,21-diisopropyl-1,4,7,10,12,15,19,25,28-nonamethyl-1,4,7,10,13,16, 19,22, 25,28,31-undecaazacyclotritriacontane-2,5,8,11, 14,17,20,23,26,29,32-unde-cone).

The term "sterile", when characterizing the compositions of the invention, means that said compositions are free from microorganisms. A sterile composition may be obtained by filtration through a 0.22 μm filter.

The term "ophthalmic", when characterizing the compositions of the invention, means that said compositions are suitable for their application to the eye. Typically, suitable compositions for application to the eye have a pH from 4.0 to 9.0, preferably from 6.8 to 7.8. In particular, ophthalmic compositions of the invention are substantially free from ocular toxic agents. Preferably, the ophthalmic compositions of the invention have an osmolality from 150 to 500 mOsm/kg, preferably 270 to 330 mOsm/kg.

The term "ocular toxic agent" refers to a compound which produces an adverse response when applied to the eye, such as visual disturbances, ocular irritation, photophobia, optic neuropathy, xanthopsia (yellow vision), cataract, corneal degeneration, corneal depositions, retinal damage, conjunctivitis, increased intraocular pressure, macular edema, allergic reactions, among others. Examples of ocular toxic agents are benzalkonium chloride, chlorobutanol, methyl paraben, sodium perborate, thimerosal and penetration enhacers such as stearylamine, oleylamine and N-[1-(2,3-dioleoyloxy)propyl]-N,N,N-trimethylammonium chloride (DOTAP).

The expression "substantially free from", as used herein, is to be interpreted as having as less than 5 wt % of a component with respect to the total weight of the composition, preferably less than 1 wt %, more preferably less than 0.5 wt %, more preferably less than 0.1 wt %, still more preferably less than 0.05 wt %, even more preferably less than 0.01 wt %, the most preferred being 0 wt %, i.e. the compound is not present in the compositions of the invention.

The term "aqueous", when characterizing the compositions of the invention, means that said compositions comprise water, preferable at least, 1 wt % of water with respect to the total weight of the composition, more preferably at least 10 wt % of water, more preferably at least 20 wt % of water, more preferably at least 30 wt % of water, more preferably at least 40 wt % of water, more preferably at least 50 wt % of water, more preferably at least 60 wt % of water, more preferably at least 70 wt % of water, more preferably at least 80 wt % of water, more preferably at least 85 wt % of water, more preferably at least 90 wt % of water. In a particularly preferred embodiment, the compositions of the present invention comprise at least 80 wt % of water with respect to the total weight of the composition.

The term "castor oil" refers to a vegetable oil obtained by pressing the seeds of the castor oil plant (*Ricinus communis*). It is a triglyceride in which approximately 90% of fatty acid chains are ricinoleate; oleate and linoleates are the other significant components. The average composition of fatty acid chains in castor oil is the following:
85%-95% of ricinoleic acid,
2%-6% of oleic acid,
1%-7% of linoleic acid,
0%-1% of linolenic acid,
0%-2.5% of stearic acid,
0.1%-2% of palmitic acid,
0.2%-1.0% of other fatty acids.

The term "medium chain triglyceride" or "MCT" refers to triesters of glycerol and $C_6$-$C_{12}$ fatty acids, examples of said fatty acids being caproic acid ($C_6$), caprylic acid ($C_8$), capric acid ($C_{10}$) and lauric acid ($C_{12}$). The three fatty acid residues of the MCT can be the same or different, preferably there are two different fatty acid residues. Preferred medium chain triglycerides are caprylic/capric acid triglyceride (marketed as Stelliesters® MCT 65/35, Estasan®, Crodamol® GTC/C, Miglyol® 812 or 810, and Neobee® M5).

In a preferred embodiment, the castor oil and the medium chain triglyceride are in a ratio by weight of from 50:1 to 1:50, preferably from 10:1 to 1:10, more preferably from 5:1 to 1:5, more preferably from 2:1 to 1:2, still more preferably from 1.5:1 to 1:1.5, even more preferably from 1.1:1 to 1:1.1, the most preferred in a ratio of 1:1.

In another preferred embodiment, the total amount of castor oil and medium chain triglyceride is from 0.05 to 100 wt %, more preferably from 0.05 to 70 wt % with respect to the total weight of the composition, preferably from 0.05 to 10%, more preferably from 2 to 5 wt %, more preferably from 0.5 to 3 wt %, still more preferably from 2 to 3 wt %, the most preferred 2.5 wt %.

In a particular embodiment, the osmolality of said composition is from 150 to 500 mOsm/kg, preferably from 270 mOsm/kg to 330 mOsm/kg.

The osmolality is a measure of the moles of solute that contribute to a solution's osmotic pressure (or osmoles) per kilogram of solvent. The osmolality may be determined using an osmometer.

The oily phase of the composition comprises the castor oil and the medium chain triglyceride, which have been defined above, and the aqueous phase comprises water.

The term "surfactant", as used herein, refers to a compound that lowers the surface tension or interfacial tension between two liquids or between a liquid and a solid. Surfactants may act as detergents, wetting agents, emulsifiers, foaming agents and dispersants. Surfactants have a hydrophobic part and a hydrophilic part. Depending on the nature of the hydrophilic part the surfactants are classified as non-ionic (surfactant with a non-charged but polar hydrophilic part), anionic (when the hydrophilic part contains a negatively charged group), cationic (when the hydrophilic part contains a positively charged group) or amphoteric (when the when the hydrophilic part contains has both cationic and anionic groups). Preferably, the one or more surfactants are non-ionic surfactants.

In a preferred embodiment, the resulting hydrophilic-lipophilic balance (HLB) value of said one or more surfactants, preferably one or more non-ionic surfactants, is from 10 to 16, preferably from 11 to 14. Thus, if only one surfactant is present in the composition, preferably a non-ionic surfactant, said surfactant is selected from those having an HLB value from 10 to 16, preferably from 11 to 14. However, if two or more surfactants are present, preferably non-ionic surfactants, said surfactants may have each an HLB value outside the range of from 11 to 14 or within said range with the proviso that the HLB value of the resulting surfactant mixture is in the range of from 10 to 16, preferably from 11 to 14.

The term "HLB" refers to the hydrophilic-lipophilic balance and is a measure of the degree to which a surfactant is hydrophilic or lipophilic. The HLB values of surfactants are widely reported in the literature [see for example Griffin, Journal of the Society of Cosmetic Chemists, 1949, 1, 311-326]. When two or more surfactants are present in the composition of the invention, the total HLB, value of the mixture of said two or more surfactants is calculated as the weight average of the HLB values of the two or more surfactants (see following equation (1)).

$$HLB_t = (\Sigma W_i \cdot HLB_i)/(\Sigma W_i) \quad \text{Equation (1)}$$

wherein $W_i$ and $HLB_i$ indicate the weight and the HLB value of the i-th surfactant, respectively.

Preferably, the one or more surfactant, preferably non-ionic surfactant, is selected from the group consisting of polyoxyl castor oil with 30 to 40 oxyethylene units, in particular polyoxyl 35 castor oil (also known as polyethylene glycol 35 castor oil; marketed as Kolliphor® EL, Cremophor® EL), polyoxyl hydrogenated castor oil with 40 to 60 oxyethylene units, in particular polyoxyl 40 hydrogenated castor oil (also known as polyethylene glycol 40 hydrogenated castor oil; marketed as Cremophor® RH40), polyoxyethylene 20 sorbitan monooleate (also known as polysorbate 80 and marketed as Tween® 80), polyoxyethylene 20 sorbitan monostearate (also known as Polysorbate 60 and marketed as Tween® 60), polyoxyethylene 20 sorbitan trioleate (marketed as Tween® 85), polyoxyethylene 20 sorbitan tristearate (marketed as Tween® 65), polyoxyethylene 20 sorbitan monolaurate (also known as Polysorbate 20), polyoxyethylene 20 sorbitan monopalmitate (also known as Polysorbate 40), sorbitan trioleate, sorbitan tristearate, sorbitan sesquioleate, sorbitan oleate, sorbitan stearate, sorbitan isostearate, sorbitan palmitate, sorbitan laurate, polyethylene glycol hexadecyl ether (marketed as Brij® C10), glyceryl stearate (marketed as Cithrol® GMS40), glyceryl monooleate, glycol stearate, glycol distearate, D-α-Tocopherol polyethylene glycol 1000 succinate (TPGS), polyoxyl steraryl ether with 2 oxyethylene units, polyoxyl castor oil with 2 to 20 oxyethylene units, cetostearyl alcohol, stearyl alcohol, and mixtures thereof. More preferably, the one or more surfactant, preferably non-ionic surfactant, is selected from the group consisting of polyoxyl 35 castor oil, polyoxyl 40 hydrogenated castor oil, polyoxyethylene 20 sorbitan monooleate, polyoxyethylene 20 sorbitan monostearate polyoxyethylene 20 sorbitan trioleate, polyoxyethylene 20 sorbitan tristearate, polyethylene glycol hexadecyl ether, glyceryl stearate, D-α-Tocopherol polyethylene glycol 1000 succinate (TPGS), and mixtures thereof. Still more preferably, the one or more non-ionic surfactant is selected from the group consisting of polyoxyl 35 castor oil, polyoxyethylene 20 sorbitan trioleate, polyethylene glycol hexadecyl ether, and mixtures thereof. Still more preferably, the one or more surfactant is selected from the group consisting of polyoxyl 35 castor oil, polyoxyethylene 20 sorbitan monooleate, sorbitan laurate, and mixtures thereof. Even more preferably, the non-ionic surfactant is polyoxyl 35 castor oil.

In a preferred embodiment, the total amount of surfactant, preferably non-ionic surfactant, is from 0.1 to 40 wt %, preferably from 3 to 40 wt %, preferably from 3 to 20 wt %, more preferably from 3 to 10 wt %, more preferably from 4 to 6 wt %, the most preferred about 5 wt % with respect to the total weight of the composition.

In a particular embodiment, the compositions of the present invention may further comprise a cosurfactant selected from the group consisting of alcohols, such as ethanol, isopropanol, n-butanol, isobutanol, 2-pentanol, isopentanol, n-pentanol, n-hexanol, 1-decanol; glycols, such as propylene glycol, 1,2-octanediol, tetraglycol, 1,2-hexandiol, polyethylene glycol; short chain fatty acids, such as sodium laurate; amines or ether-alcohols, such as diethylene glycol monoethyl ether.

In another preferred embodiment, the compositions of the present invention further comprise one or more oils other than the castor oil and the medium chain triglyceride. Preferably said one or more oil other than the castor oil and the medium chain triglyceride is selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triethylhexanoin, isohexadecane, mineral oil, vegetable oil, in particular argan oil, triisononanoin, $C_{12-15}$ alkyl benzoate, and mixtures thereof. More preferably said one or more oil other than the castor oil and the medium chain triglyceride is selected from the group consisting of ethyl oleate, isopropyl myristate, isopropyl palmitate, isopropyl isostearate, isostearyl isostearate, argan oil, triisononanoin, $C_{12-15}$ alkyl benzoate, and mixtures thereof.

The term "vegetable oil" refers to a triglyceride extracted from a plant. Examples of vegetable oils are argan oil, corn oil, palm oil, coconut oil, cottonseed oil, olive oil, peanut oil, rapeseed oil, sunflower oil, sesame oil, soybean oil, safflower oil, and the like.

The term "$C_{12-15}$ alkyl" refers to a linear or branched saturated monovalent hydrocarbon chain containing 12 to 15 carbon atoms, such as dodecyl, tridecyl, tetradecyl, pentadecyl, etc.

In another preferred embodiment, the compositions of the present invention further comprise one or more tonicity adjusting agents. Said tonicity adjusting agents are used for adjusting the osmolality of the compositions of the invention, preferably to an osmolality of from 150 to 500 mOsm/kg, preferably 270 to 330 mOsm/kg. Preferably said one or more tonicity adjusting agent is selected from the group consisting of sodium chloride, potassium chloride, calcium chloride, sodium phosphate, potassium phosphate, sodium bicarbonate (also known as sodium hydrogen carbonate), calcium carbonate, sodium lactate, sorbitol, mannitol, xylitol, glycerin, dextrose, polyethylene glycol, propylene glycol, dextran, and mixtures thereof. More preferably said one or more tonicity adjusting agent is selected from the group consisting of sodium chloride, glycerin, propylene glycol, and mixtures thereof. Still more preferably said one or more tonicity adjusting agent is glycerin. In a particular embodiment, the tonicity adjusting agent is present in an amount of 0.05 to 15 wt % with respect to the total weight of the composition.

In another preferred embodiment, the compositions of the present invention further comprise one or more pH adjusting agents. Said pH adjusting agents are used for adjusting the pH of the compositions of the invention, preferably to a pH of from 5.0 to 9.0, more preferably to a pH of from 6.8 to 7.8. Preferably wherein the one or more pH adjusting agent is selected from the group consisting of lactic acid and salts thereof (such as sodium lactate, potassium lactate and calcium lactate), citric acid and salts thereof (such as sodium citrate, potassium citrate, calcium citrate and lithium citrate), tartaric acid and salts thereof (such as sodium tartrate potassium tartrate, calcium tartrate and lithium tartrate), acetic acid and salts thereof (such as sodium acetate, potassium acetate and calcium acetate), hydrochloric acid, boric acid and salts thereof (sodium borate), sulphuric acid and salts thereof (such as sodium sulphate and potassium sulphate), nitric acid, hydrochloric acid, phosphoric acid and salts thereof (such as sodium dihydrogen phosphate, sodium monohydrogen phosphate, potassium dihidrogen phosphate lithium phosphate, potassium phosphate and calcium phosphate), carbonic acid and salts thereof (such as sodium carbonate, sodium hydrogen carbonate and potassium hydrogen carbonate), maleic acid and salts thereof (lithium maleate, sodium maleate, potassium maleate and calcium maleate), succinic acid and salts thereof (lithium succinate, sodium succinate, potassium succinate and calcium succinate), sodium hydroxide, potassium hydroxide, triethanolamine, diisopropanolamine, ammonia, tris(hydroxymethyl)aminomethane, tris(hydroxymethyl)aminomethane hydrochloride, and mixtures thereof. More preferably wherein the one or more pH adjusting agent is selected from the group consisting of tris(hydroxymethyl)aminomethane, tris(hydroxymethyl)aminomethane hydrochloride, potassium dihydrogen phosphate, disodium hydrogen phosphate, and mixtures thereof. In a particular embodiment, the pH adjusting agent is present in an amount of 0.01 to 2.5 wt % with respect to the total weight of the composition.

In a preferred embodiment, the compositions of the present invention further comprise one or more active ingredients selected from the group consisting of retinyl acetate (vitamin A), retinyl palmitate, retinyl propionate, cyanocobalamin, ergocalciferol (Vitamin D2), cholecalciferol (Vitamin D3), tocopherol, tocopheryl acetate, cranberry extract, blueberry extract, bilberry extract, aloe vera extract, flaxseed oil, maquiberry extract, resveratrol, caffeine, and mixtures thereof. Preferably, the one or more active ingredients comprised in the compositions of the present invention is selected from the group consisting of cranberry extract, maquiberry extract, retinyl acetate, retinyl palmitate, retinyl propionate, cholecalciferol, ergocalciferol, tocopheryl acetate, and mixtures thereof. In a particular embodiment, the active agent is present in an amount of 0 to 5 wt % with respect to the total weight of the composition.

The term "extract" refers to a product prepared by extraction from the corresponding berry or plant. The extract may be in the form of a solution in a solvent, or the extract may be a concentrate or essence which is free of, or substantially free of solvent. The term extract may be a single extract obtained from a particular extraction step or series of extraction steps or the extract also may be a combination of extracts obtained from separate extraction steps. For example, a cranberry, blueberry, bilberry, maquiberry or aloe vera extract may be obtained by extracting cranberry fruit, maquiberry, blueberry, bilberry fruit or aloe vera leaves, respectively, with alcohol (such as ethanol) in water, while another cranberry, blueberry, bilberry, maquiberry or aloe vera extract may be obtained by super critical carbon dioxide extraction of cranberry fruit, blueberry, bilberry, maquiberry fruit or aloe vera leaves, respectively. Optionally, these extracts may then be combined to form another cranberry, blueberry, bilberry, maquiberry or aloe vera extract. Such combined cranberry, blueberry, bilberry, maquiberry or aloe vera extracts are also encompassed.

Preferably, the term "cranberry extract" refers to extracts from *Vaccinium macrocarpon* L. berries.

Preferably, the term "maquiberry extract" refers to extracts form *Aristotelia Chilensis* berries.

Preferably, the term "blueberry extract" refers to extracts from *Vaccinium corymbosum* berries.

Preferably, the term "bilberry extract" refers to extracts from *Vaccinium myrtillus* L., *Vaccinium uliginosum* L., *Vaccinium caespitosum*, *Vaccinium deliciosum*, *Vaccinium membranaceum* and/or *Vaccinium ovalifolium* berries.

Preferably, the term "aloe vera extract" refers to *Aloe barbadensis* leaf extract and leaf juice.

The compositions of the present invention may also comprise viscosity increasing agents, preservatives, chelating agents and/or penetration enhancers.

The term "viscosity increasing agent" refers to a substance which can increase the viscosity of the compositions of the invention. Examples of viscosity increasing agents are polyvinylpirrolidones, such as Povidone K 17, Povidone K25, Povidone K 30 and Povidone K 90F; polyvinyl alcohol; xanthan gum; guar gum; welan gum; gellan gum; tragacanth gum; ceratonia gum; agar; methylcellulose; ethylcellulose; hydroxyethyl cellulose; hydroxyethylmethyl cellulose; hydroxypropyl cellulose; hydroxypropylmethyl cellulose; hydroxypropylmethyl cellulose phthalate; hydroxypropylmethyl cellulose acetate succinate; sodium carboxymethylcellulose; calcium carboxymethylcellulose; polyethylene glycol; glycerine; carrageenan; alginic acid; sodium alginate; potassium alginate; propylene glycol alginate; hyaluronic acid; sodium hyaluronate; poly(acrylic acid) derivatives such as carbomer and polycarbol; poloxamers; chitosan and chitosan derivatives; maltodextrin; and mixtures thereof.

The term "polyvinylpyrrolidone", "PVP" or "povidone" refers to a water-soluble polymer made from the monomer N-vinylpyrrolidone. The molecular weight of polyvinylpyrrolidone can vary within a wide range; nevertheless, in a particular embodiment, the molecular weight of the polyvinylpyrrolidone used in the compositions of the invention is comprised between 2.5 and 1000 kDa, typically between 10 and 1000 kDa.

The term "gellan gum" refers to a water-soluble anionic polysaccharide produced by the bacterium *Sphingomonas elodea*. The repeating unit of the polymer is a tetrasacharide, which consists of two residues of D-glucose, one residue of L-rhamnose and one residue of D-glucuronic acid. The molecular weight of gellan gum can vary within a wide range; nevertheless, in a particular embodiment, the molecular weight of gellan gum used in the compositions of the invention is comprised between $0.2 \cdot 10^6$ and $2 \cdot 10^6$ Da, typically between $0.2 \cdot 10^6$ and $0.3 \cdot 10^6$ Da.

The term "chitosan" refers to a linear polysaccharide composed of randomly distributed β-(1-4)-linked D-glucosamine (deacetylated unit) and N-acetyl-D-glucosamine (acetylated unit). The degree of deacetylation in a chitosan sample therefore refers to the content of free amino groups in the subunits of the polysaccharide Generally, the degree of deacetylation of commercial chitosan is equal to or greater than 40%, preferably equal to or greater than 60%. The molecular weight of chitosan can vary within a wide range; nevertheless, in a particular embodiment, the molecular weight of the chitosan used in the compositions of the invention is comprised between 5 and 5000 kDa, typically between 25 and 3000, more preferably between 50 and 1000 kDa.

A "derivative of chitosan" is to be understood as a chitosan in which one or more hydroxyl groups and/or one or more amino groups have been modified. These derivatives include, among others, acetylated (carboxymethylated), alkylated or sulfonated chitosans, as well as thiolated derivatives. A particularly preferred chitosan derivative is carboxymethyl chitosan, wherein the amino and/or hydroxyl groups present in chitosan have been partially modified by introduction of a carboxymethyl group ($CH_3$—C(=O)—), preferably wherein the carboxymethyl chitosan is N-carboxymethyl chitosan (i.e. wherein the amino groups present in chitosan have been partially modified by introduction of a carboxymethyl group).

In a particular embodiment, the compositions of the invention comprise a viscosity increasing agent, preferably selected from the group consisting of carboxymethyl chitosan, gellan gum, polyvinylpyrrolidone and sodium alginate.

In a particular embodiment, the viscosity increasing agent is present in an amount of from 0.1 to 10 wt % with respect to the total weight of the compositions, preferably from 0.2 to 5 wt %, with respect to the total weight of the composition.

The term "preservative" refers to substances formulated in the compositions of the invention to prevent microbial contamination thereof. Examples of preservatives are benzalkonium chloride, bezethonium chloride, chlorhexidine, benzyl alcohol, chlorobutanol, 2-phenylethanol, propylparaben, methylparaben, phenylmercuric acetate, phenylmercuric borate, phenylmercuric nitrate, cetyl pyridinium chloride, benzyl bromide, sodium perborate and thimerosal.

Alternatively, the compositions of the invention are devoid of preservatives; preferably they are devoid of benzalkonium chloride, thimerosal, benzethonium chloride, cetyl pyridinium chloride, benzyl bromide, chlorhexidine and/or sodium perborate; more preferably, the compositions of the invention are devoid of benzalkonium chloride.

The term "chelating agent" refers to a substance that coordinates with a metal ion. Examples of chelating agents are citric acid, in particular citric acid monohydrate, EDTA (ethylenediaminetetraacetic acid) and its salts, such as dipotassium EDTA, disodium EDTA, calcium disodium EDTA, sodium EDTA and trisodium EDTA, fumaric acid, malic acid, and maltol.

The term "penetration enhancer", as used herein, refers to a substance which enhances ocular drug penetration. Examples of penetration enhancers are surfactants such as sorbitan monolaurate, sorbitan monopalmitate, sorbitan trioleate, polyoxyethylene 20 sorbitan monolaurate, polyoxyethylene 20 sorbitan monopalmitate, polyoxyethylene 5 sorbitan monooleate, polyoxyethylene 20 sorbitan trioleate, polyoxyethylene 9 lauryl ether, polyoxyethylene 23 lauryl ether, polyoxyethylene 20 cetyl ether, polyoxyethylene 20 oleyl ether, polyethylene glycol octadecyl ether, polyoxyethylene 40 stearate, polyoxyethylene 50 stearate, palmitoyl carnitine, sodium caprate, sodium dodecyl sulfate, bile acids such as deoxycholic acid, taurocholic acid, taurodeoxycholic acid, urodeoxycholic acid, and tauroursodeoxycholic acid, fatty acids such as capric acid, caprylic and oleic acid, preservatives such as benzalkonium chloride, chlorhexidine digluconate, benzyl alcohol, chlorbutanol, 2-phenylethanol, paraben, propyl paraben and methyl paraben, EDTA, 1-dodecylazacycloheptan-2-one (Azone), hexamethylene lauramide, hexamethylene octanamide, decylmethylsulfoxide, saponin, cyclodextrins, pz-peptide, α-amino acid, cetylpyridinium chloride, cytochalasins, ionophores or mixtures thereof.

The compositions of the invention may also comprise further ingredients such as lanolin, white wax and/or petrolatum.

The term "white wax" refers to a chemically bleached form of yellow wax. Its CAS number is 8012-89-3.

The term "petrolatum" refers to a purified mixture of semisolid saturated hydrocarbons having the general formula $C_nH_{2n+2}$, which may be obtained from petroleum. Its CAS number is 8009-03-8.

In the context of the present invention, the expression "one or more" refers to 1, 2, 3, 4 or 5, preferably to 1, 2, 3 or 4, more preferably to 1, 2 or 3, and even more preferably to 1 or 2.

In a preferred embodiment, the compositions of the invention are in the form of a nanoemulsion, preferably an O/W nanoemulsion.

The term "nanoemulsion" refers to a colloidal dispersion comprising droplets having an average size from 10 to 500 nm, preferably from 20 to 200 nm. The term "average size" or "mean size", as used herein, relates to the average diameter of the droplets. The average size of these systems can be measured by standard processes known by persons skilled in the art such as dynamic light scattering. The Brownian motion of the droplets causes light to be scattered at different intensities. Analysis of the intensity fluctuations yield the velocity of the Brownian motion and hence the particle size using the Stokes-Einstein relationship. Light scattering experiments measure the scattered intensity over a range of scattering angles, θ, relative to the incident beam [Cotton, J. P. 1991. Introduction to scattering methods. In Neutron, X-Ray and Light Scattering: Introduction to an Investigative Tool for Colloidal and Polymeric Systems. Lindner, P., and Zemb, T. (eds.). Elsevier Science Publishing Company, Inc., New York. 3-18]. In a preferred embodiment, the light scattered is detected at 173°, known as Backscattered detection or non-Invasive back scatter technology (NIBS) by means of a Zetasizer Nano ZS (Malvern Instruments).

The nanoemulsions of the invention comprise a liquid phase (such as an oily phase or an aqueous phase) dispersed in another liquid phase (such as an aqueous phase or an oily phase, respectively) and a surfactant, wherein said liquid phases are immiscible. The nanoemulsions of the invention allow administration of hydrophobic and hydrophilic active agents since they comprise both hydrophobic and hydrophilic domains (i.e. aqueous phase and oily phase). One advantage related to the use of nanoemulsions is that they can be prepared with low amounts of surfactants, thus, reducing their potential irritating effect when administered to the eye. Moreover, some non-ionic surfactants, such as polyethylene derivatives, may inhibit the action of the glycoprotein-P (gp-P) enzyme present in the epithelial cells of the ocular surface, thus improving the corneal transport of the nanoemulsion's components. Nanoemulsions may also interact with the lipidic layer present in the tear film, thus, staying in the conjunctival sac for a longer period and acting as a reservoir of active agents.

In a particular embodiment, the composition of the invention comprises:
- from 0 to 5 wt % of an active ingredient selected from the group consisting of retinyl acetate, retinyl palmitate, retinyl propionate, cyanocobalamin, cholecalciferol, ergocalciferol, tocopherol, tocopheryl acetate, cranberry extract, blueberry extract, bilberry extract, maquiberry extract, and mixtures thereof;
- from 0.1 to 40 wt % of a surfactant selected form the group consisting of polyoxyl castor oil with 30 to 40 oxyethylene units, TPGS, polyoxyethylene 20 sorbitan monolaurate, polyoxyethylene 20 sorbitan monopalmitate, polyoxyethylene 20 sorbitan monostearate, polyoxyethylene 20 sorbitan tristearate, polyoxyethylene 20 sorbitan monooleate, polyoxyethylene 20 sorbitan trioleate, polyoxyl hydrogenated castor oil with 40 to 60 oxyethylene units, and mixtures thereof;
- from 0.1 to 70 wt % of an oil mixture comprising castor oil and medium chain triglycerides, and optionally also comprising an oil other than castor oil and medium chain triglyceride selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triisononanoin, $C_{12\text{-}15}$ alkyl benzoate, triethylhexanoin, isohexadecane, mineral oil, vegetable oil, and mixtures thereof;
- from 0 to 20 wt % of a cosurfactant selected from the group consisting of alcohols such as ethanol, isopropanol, isobutanol, n-butanol, 2-pentanol, isopentanol, n-pentanol, n-hexanol, 1-decanol, glycols such as propylene glycol, 1,2 octanodiol, tetraglycol, 1,2 hexandiol, polyethylene glycol, short chain fatty acids such as sodium laurate, amines or ether-alcohols such as diethylene glycol monoethyl ether, and mixtures thereof;
- optionally a tonicity adjusting agent, a pH adjusting agent, a viscosity increasing agent, a preservative, a chelating agent, and/or a penetration enhancer; and
- up to 100 wt % of water;

wherein the wt % is expressed with respect to the total weight of the composition.

In another particular embodiment, the composition of the invention comprises:
- from 0 to 5 wt % of an active ingredient selected from the group consisting of retinyl acetate, retinyl palmitate, retinyl propionate, cyanocobalamin, cholecalciferol, ergocalciferol, tocopherol, tocopheryl acetate, cranberry extract, blueberry extract, bilberry extract, maquiberry extract, and mixtures thereof;
- from 0.1 to 25 wt % of a surfactant selected form the group consisting of polyoxyl castor oil with 30 to 40 oxyethylene units, TPGS, polyoxyethylene 20 sorbitan monolaurate, polyoxyethylene 20 sorbitan monopalmitate, polyoxyethylene 20 sorbitan monostearate, polyoxyethylene 20 sorbitan tristearate, polyoxyethylene 20 sorbitan monooleate, polyoxyethylene 20 sorbitan trioleate, polyoxyl hydrogenated castor oil with 40 to 60 oxyethylene units, and mixtures thereof;
- from 0.1 to 50 wt % of an oil mixture comprising castor oil and medium chain triglycerides, and optionally also comprising an oil other than castor oil and medium chain triglyceride selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triisononanoin, $C_{12\text{-}15}$ alkyl benzoate, triethylhexanoin, isohexadecane, mineral oil, and mixtures thereof;
- optionally a tonicity adjusting agent, a pH adjusting agent, a viscosity increasing agent, a preservative, a chelating agent, and/or a penetration enhancer; and
- up to 100 wt % of water;

wherein the wt % is expressed with respect to the total weight of the composition.

In another particular embodiment, the composition of the invention comprises:
- from 0 to 5 wt % of an active ingredient selected from the group consisting of retinyl acetate, retinyl palmitate, retinyl propionate, cyanocobalamin, cholecalciferol, ergocalciferol, tocopherol, tocopheryl acetate, cranberry extract, blueberry extract, bilberry extract, maquiberry extract, and mixtures thereof;
- from 0.1 to 25 wt % of a surfactant selected form the group consisting of sorbitan trioleate, sorbitan tristearate, sorbitan sesquiolate, sorbitan oleate, sorbitan stearate, sorbitan isostearate, sorbitan palmitate, sorbitan laurate, glycol stearate, glycol distearate, glycerol monooleate, glycerol monosterate, polyoxyl steraryl ether with 2 oxyethylene units, polyoxyl castor oil with 2 to 20 oxyethylene units, and mixtures thereof;
- from 0.1 to 50 wt % of an oil mixture comprising castor oil and medium chain triglycerides, and optionally also comprising an oil other than castor oil and medium chain triglyceride selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triisononanoin, $C_{12\text{-}15}$ alkyl benzoate, triethylhexanoin, isohexadecane, mineral oil, and mixtures thereof;
- optionally a tonicity adjusting agent, a pH adjusting agent, a viscosity increasing agent, a preservative, a chelating agent, and/or a penetration enhancer; and
- up to 100 wt % of water;

wherein the wt % is expressed with respect to the total weight of the composition.

In another particular embodiment, the composition of the invention comprises:
- from 0 to 5 wt % of an active ingredient selected from the group consisting of retinyl acetate, retinyl palmitate, retinyl propionate, cyanocobalamin, cholecalciferol, ergocalciferol, tocopherol, tocopheryl acetate, cranberry extract, blueberry extract, bilberry extract, maquiberry extract, and mixtures thereof;
- from 0 to 5 wt % of a surfactant selected form the group consisting of sorbitan trioleate, sorbitan tristearate, sorbitan sesquiolate, sorbitan oleate, sorbitan stearate, sorbitan isostearate, sorbitan palmitate, sorbitan laurate, glycol stearate, glycol distearate, glycerol monooleate, glycerol monosterate, polyoxyl stearayl ether with 2 oxyethylene units, polyoxyl castor oil with 2 to 20 oxyethylene units, polyoxyl castor oil with 30 to 40 oxyethylene units, TPGS, polyoxyethylene 20 sorbitan monolaurate, polyoxyethylene 20 sorbitan monopalmitate, polyoxyethylene 20 sorbitan monostearate, polyoxyethylene 20 sorbitan tristearate, polyoxyethylene 20 sorbitan monooleate, polyoxyethylene 20 sorbitan trioleate, polyoxyl hydrogenated castor oil with 40 to 60 oxyethylene unit and mixtures thereof;

from 0 to 20 wt % of a viscosity increasing agent selected from the group consisting of hydroxypropyl cellulose, ethyl cellulose, hydroxypropylmethyl cellulose phthalate, hydroxypropylmethyl cellulose acetate succinate and mixtures thereof;

from 0 to 5 wt %, preferably from 1 to 5 wt % of water; and up to 100 wt % of an oil mixture comprising castor oil and medium chain triglycerides, and optionally also comprising an oil other than castor oil and medium chain triglyceride selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triisononanoin, $C_{12-15}$ alkyl benzoate, triethylhexanoin, isohexadecane, mineral oil, vegetable oil and mixtures thereof;

wherein the wt % is expressed with respect to the total weight of the composition.

In another particular embodiment, the composition of the invention comprises:

from 0 to 5 wt % of an active ingredient selected from the group consisting of retinyl acetate, retinyl palmitate, retinyl propionate, cyanocobalamin, cholecalciferol, ergocalciferol, tocopherol, tocopheryl acetate, cranberry extract, blueberry extract, bilberry extract, maquiberry extract, and mixtures thereof;

from 0.1 to 40 wt % of a surfactant selected form the group consisting of polyoxyl castor oil with 30 to 40 oxyethylene units, TPGS, polyoxyethylene 20 sorbitan monolaurate, polyoxyethylene 20 sorbitan monopalmitate, polyoxyethylene 20 sorbitan monostearate, polyoxyethylene 20 sorbitan tristearate, polyoxyethylene 20 sorbitan monooleate, polyoxyethylene 20 sorbitan trioleate, polyoxyl hydrogenated castor oil with 40 to 60 oxyethylene unit, and mixtures thereof;

from 0.1 to 70 wt % of an oil mixture comprising castor oil and medium chain triglycerides, and optionally also comprising an oil other than castor oil and medium chain triglyceride selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triisononanoin, $C_{12-15}$ alkyl benzoate, triethylhexanoin, isohexadecane, mineral oil, vegetable oil, and mixtures thereof;

from 0 to 20 wt % of a cosurfactant selected from the group consisting of alcohols such as ethanol, isopropanol, isobutanol, n-butanol, 2-pentanol, isopentanol, n-pentanol, n-hexanol, 1-decanol, glycols such as propylene glycol, 1,2 octanodiol, tetraglycol, 1,2 hexandiol, polyethylene glycol, short chain fatty acids such as sodium laurate, amines or ether-alcohols such as diethylene glycol monoethyl ether, and mixtures thereof;

from 0.2 to 20 wt % of a viscosity increasing agent selected from the group consisting of polyvinylpirrolidone, such as Povidone K 17, Povidone K25, Povidone K 30 and Povidone K 90F; polyvinyl alcohol, xanthan gum, guar gum, welan gum, gellan gum, tragacanth gum, ceratonia gum, agar, methylcellulose, ethylcellulose, hydroxyethyl cellulose, hydroxyethylmethyl cellulose, hydroxypropyl cellulose, hydroxypropylmethyl cellulose sodium carboxymethylcellulose, calcium carboxymethylcellulose, sodium carboxymethylcellulose, polyethylene glycol, glycerin, carrageenan, alginic acid, sodium alginate, potassium alginate, propylene glycol alginate, hyaluronic acid, sodium hyaluronate, poly(acrylic acid) derivatives such as carbomer and polycarbol, poloxamers, chitosan and chitosan derivatives, maltodextrin, and their mixtures thereof;

optionally a tonicity adjusting agent, a pH adjusting agent, a preservative, a chelating agent, and/or a penetration enhancer; and up to 100 wt % of water;

wherein the wt % is expressed with respect to the total weight of the composition.

In another particular embodiment, the composition of the invention comprises:

from 0 to 5 wt % of an active ingredient selected from the group consisting of retinyl acetate, retinyl palmitate, retinyl propionate, cyanocobalamin, cholecalciferol, ergocalciferol, tocopherol, tocopheryl acetate, cranberry extract, blueberry extract, bilberry extract, maquiberry extract, and mixtures thereof;

from 0 to 25 wt % of a surfactant selected form the group consisting of sorbitan trioleate, sorbitan tristearate, sorbitan sesquiolate, sorbitan oleate, sorbitan stearate, sorbitan isostearate, sorbitan palmitate, sorbitan laurate, glycol stearate, glycol distearate, glycerol monooleate, glycerol monosterate, polyoxyl stearayl ether with 2 oxyethylene units, polyoxyl castor oil with 2 to 20 oxyethylene units, polyoxyl castor oil with 30 to 40 oxyethylene units, TPGS, polyoxyethylene 20 sorbitan monolaurate, polyoxyethylene 20 sorbitan monopalmitate, polyoxyethylene 20 sorbitan monostearate, polyoxyethylene 20 sorbitan tristearate, polyoxyethylene 20 sorbitan monooleate, polyoxyethylene 20 sorbitan trioleate, polyoxyl hydrogenated castor oil with 40 to 60 oxyethylene, cetosterayl alcohol, stearyl alcohol, and mixtures thereof;

from 0.1 to 70 wt % of an oil mixture comprising castor oil and medium chain triglycerides, and optionally also comprising an oil other than castor oil and medium chain triglyceride selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triisononanoin, $C_{12-15}$ alkyl benzoate, triethylhexanoin, isohexadecane, mineral oil, vegetable oil, and mixtures thereof;

from 0 to 20 wt % of a cosurfactant selected from the group consisting of alcohols such as ethanol, isopropanol, isobutanol, n-butanol, 2-pentanol, isopentanol, n-pentanol, n-hexanol, 1-decanol, glycols such as propylene glycol, 1,2 octanodiol, tetraglycol, 1,2 hexandiol, polyethylene glycol, short chain fatty acids such as sodium laurate, amines or ether-alcohols such as diethylene glycol monoethyl ether, and mixtures thereof;
optionally a tonicity adjusting agent, a pH adjusting agent, a viscosity increasing agent, a preservative, a chelating agent, and/or a penetration enhancer;
from 0 to 25 wt % of lanolin;
from 0 to 25 wt % of white wax;
from 0 to 50 wt % of water; preferably from 1 to 50% and up to 100 of petrolatum;
wherein the wt % is expressed with respect to the total weight of the composition.

In another particular embodiment, the composition of the invention comprises:
a medium chain triglyceride;
castor oil;
a surfactant selected from the group consisting of polyoxyl 35 castor oil, polyoxyethylene 20 sorbitan monooleate, sorbitan laurate, and mixtures thereof;
optionally an active ingredient selected from the group consisting of cranberry extract, maquiberry extract, retinyl acetate, retinyl palmitate, retinyl propionate, cholecalciferol, ergocalciferol, tocopheryl acetate, and mixtures thereof;
optionally a pH adjusting agent selected from the group consisting of tris(hydroxymethyl)aminomethane, tris(hydroxymethyl)aminomethane hydrochloride, potassium dihydrogen phosphate, disodium hydrogen phosphate, and mixtures thereof;
a tonicity adjusting agent selected from the group consisting of glycerine, propylene glycol, sodium chloride, and mixtures thereof;
optionally a polymer selected from the group consisting of carboxymethyl chitosan, gellan gum, polyvinylpyrrolidone and mixtures thereof;
optionally sodium alginate; and
water.

In another particular embodiment, the composition of the invention comprises:
from 0.3 to 2.6 wt % of a medium chain triglyceride;
from 0.3 to 2.6 wt % of castor oil;
from 0.5 to 16 wt % of a surfactant selected from the group consisting of polyoxyl 35 castor oil, polyoxyethylene 20 sorbitan monooleate, sorbitan laurate, and mixtures thereof;
optionally from 0.01 to 5 wt % of an active ingredient selected from the group consisting of cranberry extract, maquiberry extract, retinyl acetate, retinyl palmitate, retinyl propionate, cholecalciferol, ergocalciferol, tocopheryl acetate, and mixtures thereof;
optionally from 0.05 to 1.2 wt % of a pH adjusting agent selected from the group consisting of tris(hydroxymethyl)aminomethane, tris(hydroxymethyl)aminomethane hydrochloride, potassium dihydrogen phosphate, disodium hydrogen phosphate, and mixtures thereof;
from 0.4 to 16 wt % of a tonicity adjusting agent selected from the group consisting of glycerine, propylene glycol, sodium chloride, and mixtures thereof;
optionally from 0.3 to 6 wt % of a polymer selected from the group consisting of carboxymethyl chitosan, gellan gum, polyvinylpyrrolidone and mixtures thereof;
optionally from 0.2 to 0.3 wt % of sodium alginate; and
up to 100 wt % of water;
wherein the wt % is expressed with respect to the total weight of the composition.

In another particular embodiment, the composition of the invention comprises:
from 0.05 to 1.5 wt % of a medium chain triglyceride;
from 0.05 to 1.5 wt % of castor oil;
from 4 to 6 wt % of a surfactant; and
water.

In another particular embodiment, the composition of the invention comprises:
1.25 wt % of a caprylic/capric triglyceride;
1.25 wt % of castor oil;
5 wt % of polyoxyl 35 castor oil; and
water.

In another particular embodiment, the composition of the invention comprises:
1.25 wt % of a medium chain triglyceride;
1.25 wt % of castor oil;
5 wt % of a surfactant; and
water.

In another particular embodiment, the composition of the invention comprises:
from 0.05 to 1.5 wt % of a caprylic/capric triglyceride;
from 0.05 to 1.5 wt % of castor oil;
from 4 to 6 wt % of polyoxyl 35 castor oil; and
water.

In the case of components belonging to two or more categories, the amount of these components is recorded in each of the two or more categories independently. For example, if a composition comprises a component which represents 0.5 wt % with respect to the total weight of the composition and that is both penetration enhancer and a preservative, it is accounted for 0.5 wt % of penetration enhancer and 0.5 wt % of preservative with respect to the total weight of the composition.

The compositions of the invention may be prepared by combining the different components described above and mixing, in particular by homogenization at high pressure when nanoemulsions are to be obtained. In particular, when the composition of the invention is in the form of a nanoemulsion, the aqueous phase is slowly added to the surfactant and oily phase mixture (which comprises at least a medium chain triglyceride and castor oil) with mixing.

Medical Uses of the Compositions of the Invention

As previously explained and as shown in the examples of the present application, the mixture of castor oil and medium chain triglyceride promotes mucin expression, in particular MUC1 and MUC5AC, and re-ephithelization. Moreover, the mixture of castor oil and medium chain triglyceride provides a synergistic effect in mucin MUC5AC and MUC1 expression and in vivo re-ephithelization, in particular in corneal wounds. Thus, the compositions of the invention are suitable for treating ophthalmic disorders related to mucin expression and re-epithelization. The compositions of the inventions are preferably administered by topical ocular route.

In view of the above, in a second aspect, the present invention relates to a sterile ophthalmic composition as defined in the first aspect for use in medicine.

This aspect may also be formulated as the use of a sterile ophthalmic composition as defined in the first aspect for the manufacture of a medicament, or as a pharmaceutical composition comprising a sterile ophthalmic composition as defined in the first aspect for use in medicine.

In a third aspect, the present invention relates to a sterile ophthalmic composition as defined in the first aspect for use in the treatment and/or prevention of an ocular disease selected from the group consisting of dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis, more particularly in the treatment and/or prevention of dry eye, blepharitis, keratitis such as filamentary keratitis and ulcerous keratitis, conjunctivitis including atopic keratoconjunctivitis, epithelial damage induced by preservatives, epithelial or anterior chamber damage induced by ocular surgery, limbal cell deficiency, corneal ulcers induced by physical or chemical agents.

This aspect may also be formulated as the use of a sterile ophthalmic composition as defined in the first aspect for the manufacture of a medicament for the treatment and/or prevention of an ocular disease selected from the group consisting of dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis, more particularly in the treatment and/or prevention of dry eye, blepharitis, keratitis such as filamentary keratitis and ulcerous keratitis, conjunctivitis including atopic keratoconjunctivitis, epithelial damage induced by preservatives, epithelial or anterior chamber damage induced by ocular surgery, limbal cell deficiency, corneal ulcers induced by physical or chemical agents.

Alternatively, this aspect may also be formulated as a method of treatment and/or prevention of an ocular disease selected from the group consisting of dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis, more particularly in the treatment and/or prevention of dry eye, blepharitis, keratitis such as filamentary keratitis and ulcerous keratitis, conjunctivitis including atopic keratoconjunctivitis, epithelial damage induced by preservatives, epithelial or anterior chamber damage induced by ocular surgery, limbal cell deficiency, corneal ulcers induced by physical or chemical agents.

The term "prevention", as used herein, refers to the administration of the composition of the invention in an initial or early stage of a disease, or to also prevent its onset.

The term "treatment" is used to designate the administration of the composition of the invention to control disorder progression before or after the clinical signs had appeared. By control of the disorder progression it is meant to designate beneficial or desired clinical results including, but not limited to, reduction of symptoms, reduction of the length of the disorder, stabilization pathological state (specifically avoidance of further deterioration), delay in the disorder's progression, improvement of the pathological state and remission (both partial and total). In a particular embodiment of the invention the composition of the invention is used to control the disorder progression once at least one of the disorder's clinical signs has appeared.

The term "medicament", as used herein, refers to a composition of the invention. The medicament may be administered by ocular topical route. It is prepared by conventional means with pharmaceutically acceptable excipients.

The term "subject", as used herein, refers to any animal or human that is suffering from one of the diseases disclosed above. Preferably, the subject is a mammal. The term "mammal", as used herein, refers to any mammalian species, including but not being limited to domestic and farm animals (cows, horses, pigs, sheep, goats, dogs, cats or rodents), primates, and humans Preferably, the mammal is a human being.

The term "preservative" as used herein as capable of inducing "epithelial damage" refers to antiseptic substances formulated in an ophthalmic composition to prevent microbial contamination of the compositions, such as benzalkonium chloride, thimerosal, benzethonium chloride, cetyl pyridinium chloride, benzyl bromide, chlorhexidine, sodium perborate, in particular benzalkonium chloride.

Examples of physical agents that may induce conical ulcers are foreign bodies such as sand, pieces of wood, metal, glass, stone, paper sheets and other materials.

Examples of chemical agents that may induce corneal ulcers are alkalis (such as NaOH, KOH, $MG(OH)_2$, $Ca(OH)_2$, $NH_3$ and the like), acids (such as $H_2SO_4$, $H_2SO_3$, HF, $CH_3COOH$, HCl, and the like), and preservatives such as benzalkonium chloride, sodium perborate sodium chloride.

Examples of ocular surgeries that may induce epithelial or anterior chamber damage are ocular anterior pole surgeries such as photorefractive keratectomy, laser in situ keratomileusis, cataract surgery, keratoplasty, trabeculectomy, refractive surgery and vitreoretinic surgery.

The invention is described below by means of several examples which do not limit, but rather illustrate the invention.

EXAMPLES

Example 1. Formulations

The compositions of formulations 1-11 are provided in Table 1 below, wherein the amount of each component is expressed in wt % with respect to the total weight of the formulations:

TABLE 1

| Component | Formulation 1 | Formulation 2 | Formulation 3 | Formulation 4 |
|---|---|---|---|---|
| MCT | 1.25 | 1.25 | 1.00 | 2.50 |
| Castor oil | 1.25 | 1.25 | 1.00 | 2.50 |
| Polyoxyl 35 castor oil | 5.00 | 5.00 | 5.00 | 15.00 |
| Tris hydroxymethyl aminomethane | 0.10 | — | 0.10 | — |
| Tris hydroxymethyl aminomethane hydrochloride | 0.66 | — | 0.66 | — |
| Potassium dihydrogen phosphate | — | 0.06 | — | 0.06 |
| Disodium hydrogen phosphate 12 hydrate | — | 1.13 | — | 1.13 |
| Glycerine | 1.50 | — | 1.50 | — |
| Propylene glycol | — | — | — | 15.00 |
| Sodium chloride | — | 0.50 | — | — |
| Polyvinylpirrolidone | 2.00 | 1.50 | — | 5.00 |
| Sodium alginate | — | — | 0.25 | — |
| Water | up to 100 | up to 100 | up to 100 | up to 100 |

| Component | Formulation 5 | Formulation 6 | Formulation 7 | Formulation 8 |
|---|---|---|---|---|
| MCT | 1.45 | 1.25 | 0.35 | 1.00 |
| Castor oil | 1.45 | 1.25 | 0.35 | 1.00 |
| Polyoxyl 35 castor oil | 7.10 | 5.00 | 6.30 | — |
| Polyoxyethylene 20 sorbitan monooleate | — | — | — | 4.25 |
| Sorbitan laurate | — | — | — | 0.50 |
| Cranberry extract | 5.00 | 0.10 | — | — |
| Maquiberry extract | — | — | — | 0.10 |
| Retinyl palmitate | 0.50 | 0.05 | 0.10 | 0.05 |
| Cholecalciferol | 0.50 | 0.001 | 0.10 | — |
| Tris hydroxymethyl aminomethane | 0.12 | 0.12 | 0.10 | 0.12 |
| Tris hydroxymethyl aminomethane hydrochloride | 0.66 | 0.66 | 0.66 | 0.66 |
| Glycerine | 1.16 | — | 1.16 | — |
| Sodium chloride | — | 0.50 | — | 0.60 |
| Carboxymethyl chitosan | 0.50 | — | — | — |
| Polyvinylpirrolidone | — | 5.00 | 2.00 | — |
| Water | up to 100 | up to 100 | up to 100 | up to 100 |

| Component | Formulation 9 | Formulation 10 | Formulation 11 |
|---|---|---|---|
| MCT | 1.00 | 1.00 | 1.00 |
| Castor oil | 1.00 | 1.00 | 1.00 |
| Polyoxyl 35 castor oil | — | 5.00 | 5.00 |
| Polyoxyethylene 20 sorbitan monooleate | 4.25 | — | — |
| Sorbitan laurate | 0.75 | — | — |
| Retinyl palmitate | 0.05 | — | — |
| Cholecalciferol | — | — | 0.10 |
| Tocopheryl acetate | 0.50 | 0.50 | 0.50 |
| Potassium dihydrogen phosphate | 0.06 | 0.06 | — |
| Disodium hydrogen phosphate 12 hydrate | 1.13 | 1.13 | — |
| Glycerine | — | — | 2.20 |
| Sodium chloride | 0.50 | 0.75 | — |
| Gellan gum | — | — | 0.35 |
| Water | up to 100 | up to 100 | up to 100 |

Example 2. Effect of Compositions Comprising Castor Oil, Medium Chain Triglycerides and Mixtures Thereof on Mucin Expression SIRC ("Staten Serum institut rabbit cornea") cells were seeded on 6 well plates at a cellular density of $5 \times 10^5$ cells/well and treated with the products to be tested as shown in table 2. The tested products were compositions comprising a total concentration of 2.5% of the oils specified in the table, 5% of a non-ionic surfactant and water. Said products comprise either castor oil (CO), the medium chain triglyceride derived from caprylic/capric acids (Stelliesters® MCT 65/35) (MCT) or both at different ratios in culture medium (i.e. MEM (minimal essential medium)+10% BFS (bovine fetal serum+1% P/S (penicillin/streptomycin)+5% kolliphor P188). For all products tested the sum of the amounts of castor oil and medium chain triglycerides was 2.5%. After 48 hours, RNA of each condition was isolated using SV Total Isolation system (Promega) according to the manufacturer's instruction. qRT-PCR was performed using a MX3000 (Stratagene) quantitative PCR system. Relative mRNA levels were quantified using One-Step qRT-PCR SYBR Green PCR Master Mix (Invitrogen) with target specific primers for genes. Primer sequences are the following: F 5'-CCCACAGAACCCAGTACAA-3' (5'-SEQ ID NO:1-3') and R 5'-AATGTGTAGCCCTCGTCT-3' (5'-SEQ ID NO:2-3') for MUC5AC and F 5'-AGGCTCAGCTTC-TACTCTGG-3' (5'-SEQ ID NO:3-3') and R 5'-GACA-GACAGCCAAGGCAATG-3' (5'-SEQ ID NO:4-3') for MUC1. Each value was normalized to β-actin (F 5'-GA-CATCAAGGAGAAGCTGTG-3' (5'-SEQ ID NO:5-3') and R 5'-AGCTCGTAGCTCTTCTCCAG-3' (5'-SEQ ID NO:6-3')). Relative changes in gene expression were calculated using the ΔCt method (Livak et al., 2001). Briefly, data were obtained as Ct values and ΔCt were determined as follow: Ct of target gene−Ct of housekeeping gene (actin). The amount of gene expression, normalized to a reference gene, is given by: $2^{\Delta Ct}$. Relative expression of MUC1 and MUC5AC mRNA in the test samples were determined as fold increase compared with the control sample (untreated cells)" using the following formula:

$$\text{Relative expression} = [2^{\Delta Ct}(\text{product}) - 2^{\Delta Ct}(\text{control})] / 2^{\Delta Ct}(\text{control})$$

TABLE 2

(products tested and figures showing results)
RATIOS CASTOR OIL (CO)/MEDIUM CHAIN
TRIGLYCERIDE (MCT) IN THE TESTED PRODUCTS 0 (only MCT)
1:50
1:10
1:5
1:1
5:1

TABLE 2-continued (products tested and figures showing results)
RATIOS CASTOR OIL (CO)/MEDIUM CHAIN
TRIGLYCERIDE (MCT) IN THE TESTED PRODUCTS 10:1
50:1
∞ (only CO)

Figure 2:
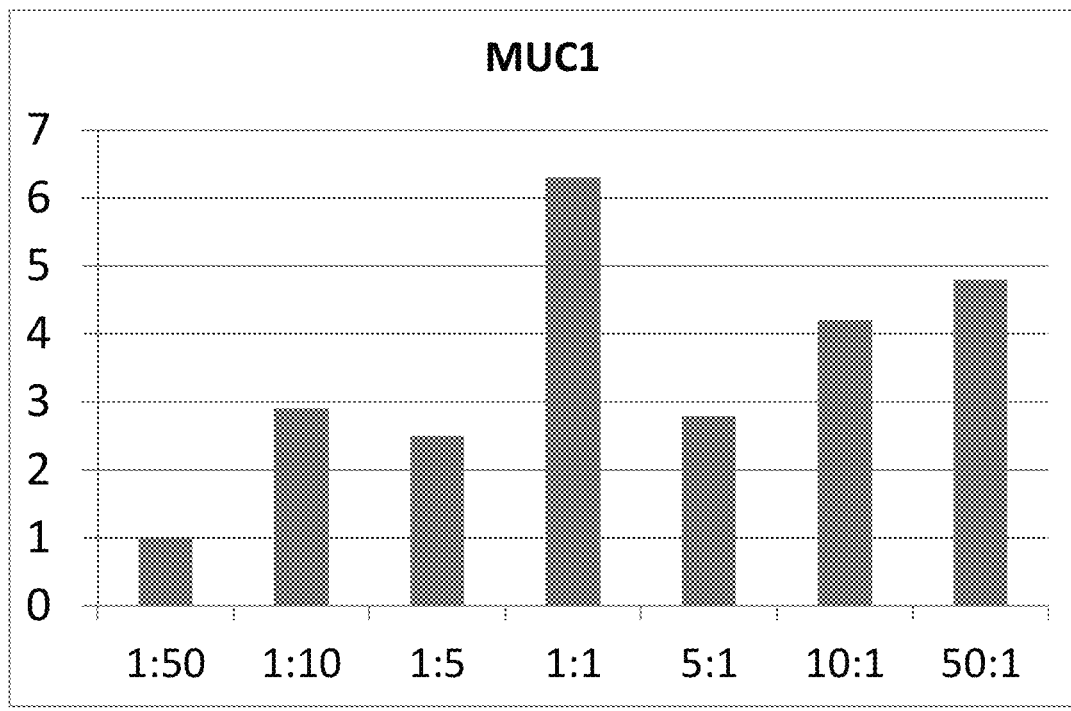
FIGS. 2 and 3 show the effect on MUC1 and MUC5AC expression of products comprising 2.5% of oils (castor oil and caprylic/capric triglyceride) at different ratios of castor oil to caprylic/capric triglyceride.

The results of relative expression of MUC1 are shown in FIG. 2 (ratios CO/MCT of 1:50, 1:10, 1:5, 1:1, 5:1, 10:1 and 50:1), 4 (comparison of product with ratio CO/MCT=50:1 and products with only one of the oils), 6 (comparison of product with ratio CO/MCT=1:1 and products with only one of the oils) and 8 (comparison of product with ratio CO/MCT=1:50 and products with only one of the oils).

Figure 3:
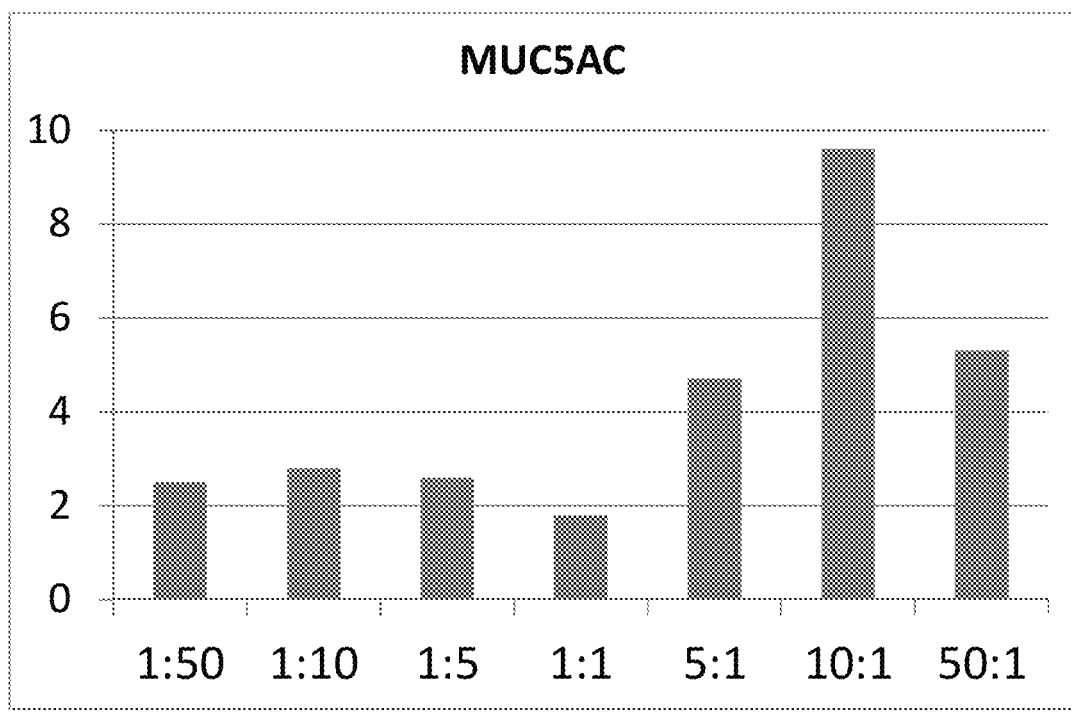
Figure 4:
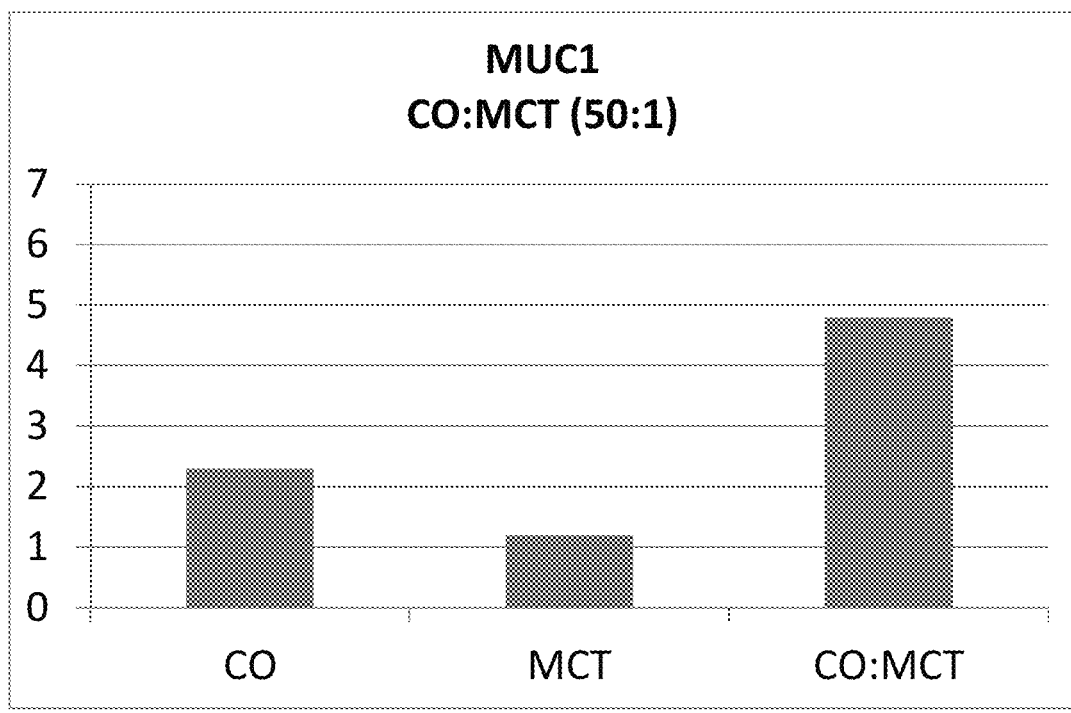
FIGS. 4 to 9 show the effect on MUC1 and MUC5AC expression of products comprising mixtures of castor oil and caprylic/capric triglyceride (at ratios of 50:1, 1:1 and 1:50) when compared with the effect of the each one of the oils alone.
Figure 5:
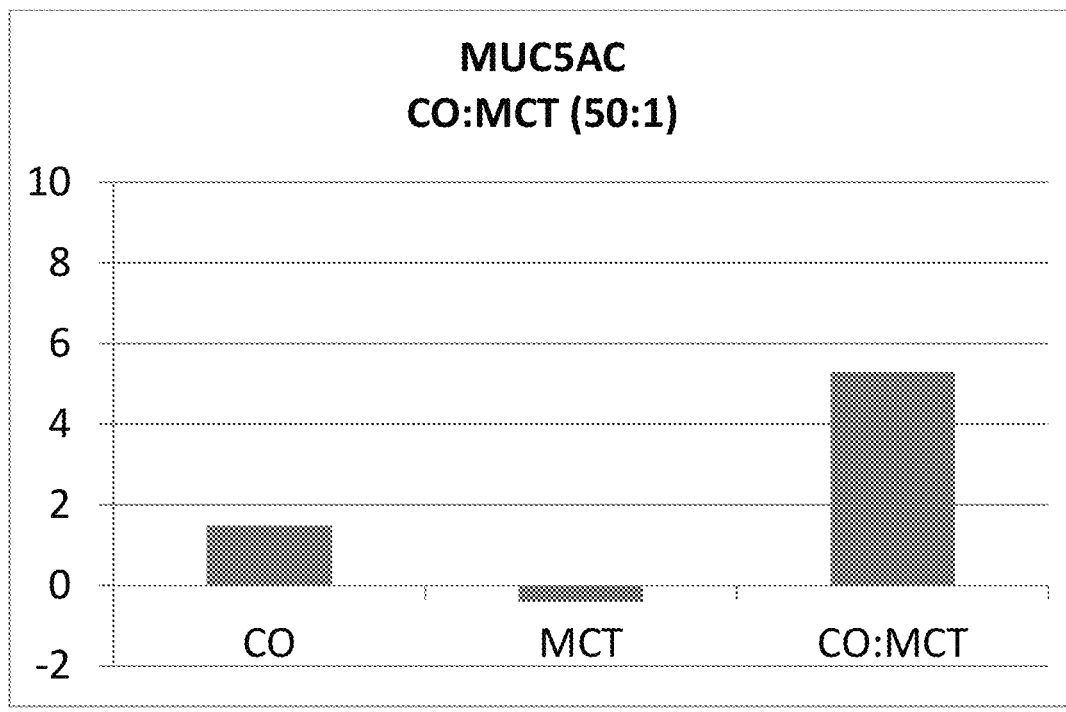
Figure 6:
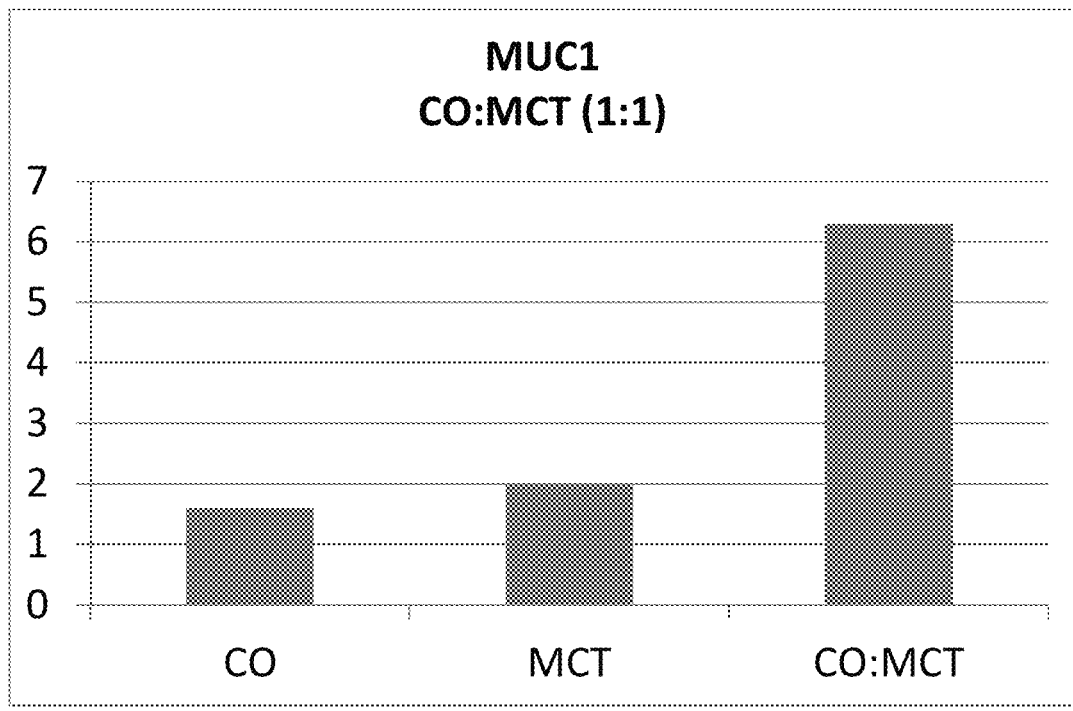
Figure 7:
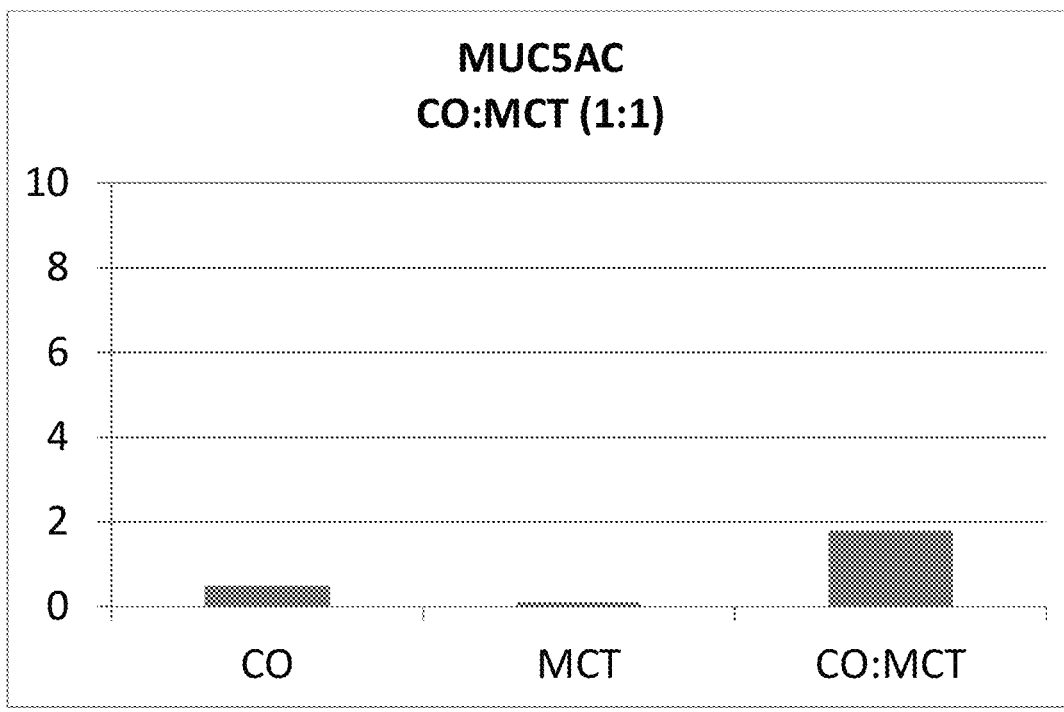
Figure 8:
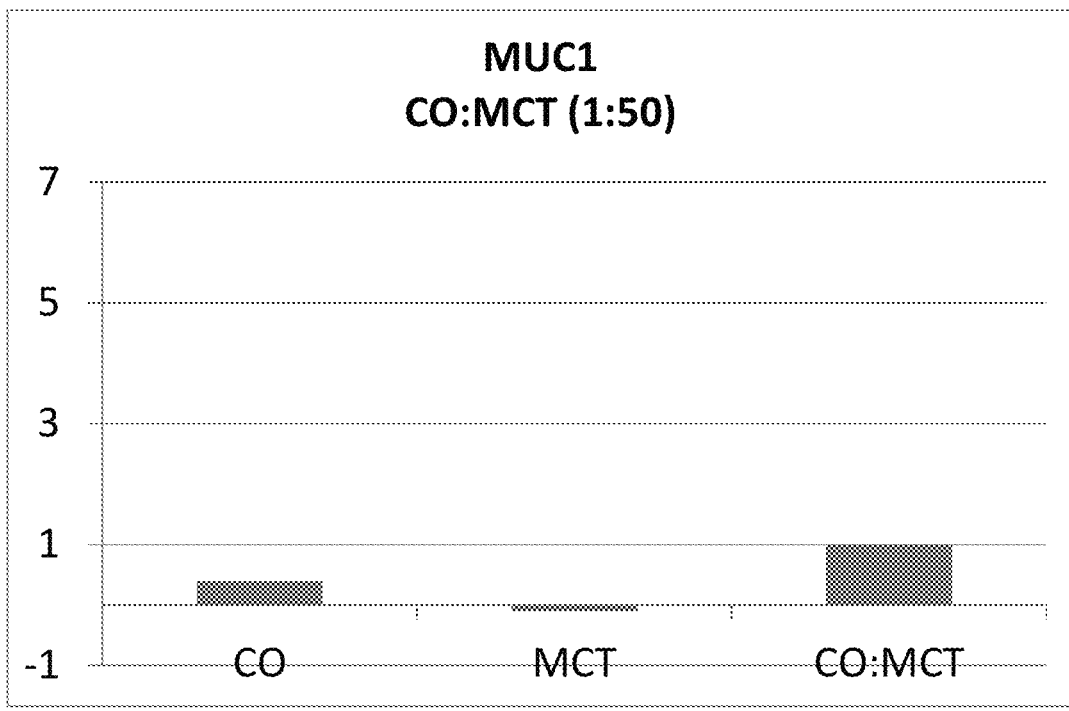
Figure 9:
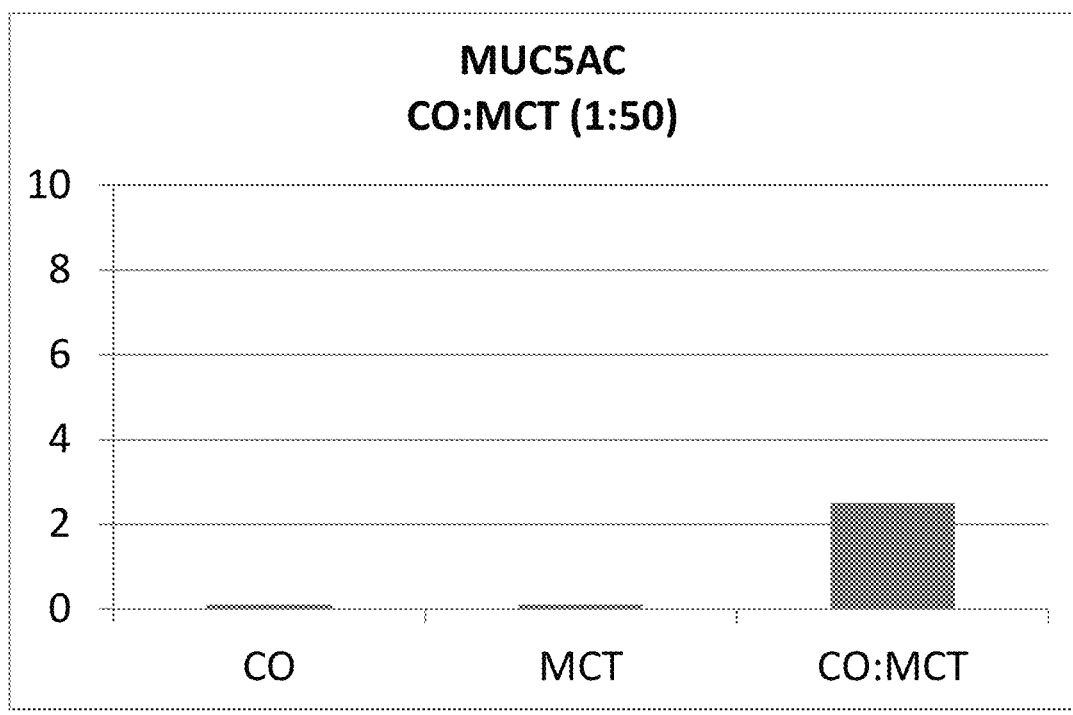

The results of relative expression of MUC5AC are shown in FIG. 3 (ratios of 1:50, 1:10, 1:5, 1:1, 5:1, 10:1 and 50:1), 5 (comparison of product with ratio CO/MCT=50:1 and products with only one of the oils), 7 (comparison of product with ratio CO/MCT=1:1 and products with only one of the oils) and 9 (comparison of product with ratio CO/MCT=1:50 and products with only one of the oils).

As can be seen from FIGS. 2 and 3 the mixture of castor oil and medium chain triglycerides (caprylic/capric triglyceride (Stelliesters® MCT 65/35) are capable of enhancing expression of MUC1 and MUC5AC at almost any ratio between the two products (results are shown over a range of ratios comprised between 1:50 and 50:1).

As can be seen from FIGS. 4 to 9, the combination of medium chain triglycerides (caprylic/capric triglyceride (Stelliesters® MCT 65/35) and castor oil has a synergistic effect in MUC1 and MUC5AC expression at almost any ratio between the two products (results are shown for ratios of 1:50, 1:1 and 50:1).

Example 3. Corneal Epithelium Wound Healing In Vivo

The formulations provided in Table 3 were used in this example (the amounts of each component are expressed in wt % with respect to the total weight of the formulations):

TABLE 3

| Component | SALINE | 2% OIL | 100% OIL |
|---|---|---|---|
| Polyoxyl 35 castor oil[a] | — | 5.00% | — |
| Caprylic/capric triglyceride[b] | — | 1.00% | 50.00% |
| Castor oil | — | 1.00% | 50.00% |
| Saline solution/water | 100% | q.s. 100% | 0% |

[a]Kolliphor ® EL
[b]Stelliesters ® MCT 65/35

Rabbits were anaesthetized by an im injection of ketamine/xylazine and both eyes were kept open by a blepharostat and anesthetized in surface by 10 µl of oxyburpocaine hydrochloride. Then a circular wound of 5 mm diameter was performed in the central corneal epithelium by applying for 30 seconds a pipette tip filled with n-heptanol soaked cotton. After that the cornea was rinsed with 10 ml of sterile saline solution. Each animal received in both eyes 40 µl of saline solution, Formulation with 2% Oil and Formulation with 100% Oil immediately and 2, 4, 6 and 8 hours after wounding. Sodium fluorescein at 1 mg/ml was applied to the ocular surface to visualize the damaged area at 15 minutes, 6, 24 and 48 hours after wounding and images were taken using a slit-lamp equipped with a blue filter. Computer analysis of the images using ImageJ was employed to determine the wound area at each time point. Wound area was defined as the ratio between fluorescein stained area and total cornea area. The % of wound area at each time was determined and, from these data, the area under the curve (AUC) was calculated for each product.

FIG. 1 represents the Area under the Curve (AUC) of % wound area vs. time after application of each one of the tested products. The lower the value the higher the healing achieved with the product. FIG. 1 shows that both 2% and 100% of an oil mixture comprised of equal weights of castor oil and medium chain triglycerides are capable of promoting wound healing (i.e. re-epithelization) more effectively than saline solution.

The invention is also related to:

[1]. Sterile ophthalmic composition comprising castor oil and a medium chain triglyceride.

[2]. Composition according to [1] characterized in that it comprises water.

[3]. Composition according to [2] comprising:
  a) an oily phase comprising castor oil and a medium chain triglyceride,
  b) one or more surfactants, and
  c) an aqueous phase;
wherein the composition has a pH from 5.0 to 9.0.

[4]. Composition according to any one of [1] to [3], wherein the castor oil and the medium chain triglyceride are in a ratio by weight of from 50:1 to 1:50, preferably from 10:1 to 1:10, more preferably from 1.5:1 to 1:1.5, more preferably 1:1.

[5]. Composition according to any one of [1] to [4], wherein the total amount of castor oil and medium chain triglyceride is from 0.05 to 70 wt % with respect to the total weight of the composition.

[6]. Composition according to any one of [1] to [4], wherein the total amount of castor oil and medium chain triglyceride is from 0.05 to 10 wt % with respect to the total weight of the composition.

[7]. Composition according to any one of [1] to [6], wherein the medium chain triglyceride is caprylic/capric acid triglyceride.

[8]. Composition according to any one of [1] to [7], further comprising one or more oils other than the castor oil and the medium chain triglyceride, preferably wherein the one or more oil other than the castor oil and the medium chain triglyceride is selected from the group consisting of ethyl oleate, isopropyl myristate, isopropyl palmitate, isopropyl isostearate, isostearyl isostearate, myristyl lactate, ethylhexyl hydroxystearate, ethylhexyl pelargonate, triethylhexanoin, isohexadecane, mineral oil, vegetable oil, in particular argan oil, triisononanoin, $C_{12-15}$ alkyl benzoate, and mixtures thereof.

[9]. Composition according to any one of [3] to [8], wherein the resulting hydrophilic-lipophilic balance value of said one or more surfactants is from 10 to 16, preferably wherein the one or more surfactant is selected from the group consisting of polyoxyl 35 castor oil, polyoxyethylene 20 sorbitan monooleate, sorbitan laurate, and mixtures thereof, more preferably wherein the surfactant is polyoxyl 35 castor oil.

[10]. Composition according to any one of [3] to [9], wherein the total amount of surfactant is from 0.1 to 40 wt % with respect to the total weight of the composition.

[11]. Composition according to any one of [3] to [10], wherein the total amount of surfactant is from 3 to 10 wt % with respect to the total weight of the composition.

[12]. Composition according to any one of [1] to [11], further comprising one or more tonicity adjusting agents, preferably wherein the one or more tonicity adjusting agent is selected from the group consisting of sodium chloride, glycerin, propylene glycol, and mixtures thereof.

[13]. Composition according to any one of [1] to [12], further comprising one or more pH adjusting agents, preferably wherein the one or more pH adjusting agent is selected from the group consisting of tris(hydroxymethyl)aminomethane, tris(hydroxymethyl)aminomethane hydrochloride, potassium dihydrogen phosphate, disodium hydrogen phosphate, and mixtures thereof.

[14]. Composition according to any one of [1] to [13], further comprising from 0.1 to 10 wt % of one or more viscosity increasing agent selected form the group consisting of sodium alginate, polyvinylpyrrolidone, gellan gum, chitosan or a derivative thereof, and mixtures thereof, with respect to the total weight of the composition.

[15]. Composition according to any one of [1] to [14], further comprising one or more active ingredients selected from the group consisting of cranberry extract, maquiberry extract, retinyl acetate, retinyl palmitate, retinyl propionate, cholecalciferol, ergocalciferol, tocopheryl acetate, and mixtures thereof.

[16]. Composition according to any one of [2] to [15], wherein the composition comprises at least 80 wt % of water with respect to the total weight of the composition.

[17]. Composition according to any one of [3] to [16], in the form of a nanoemulsion.

[18]. Composition as defined in any one of [1] to [17] for use in medicine.

[19]. Composition as defined in any one of [1] to [17] for use in the treatment and/or prevention of an ocular disease susceptible of improving by induction of the production of mucines or by promotion or re-epithelization of the eye surface.

[20]. Composition as defined in [19] for use in the treatment and/or prevention of an ocular disease selected from the group consisting of dry eye (including keratoconjunctivitis sicca, xerophthalmia, xerosis and Sjögren's syndrome), conjunctivitis (including allergic conjunctivitis, vernal keratoconjunctivitis, atopic keratoconjunctivitis, pemphigoid, Stevens-Johnson syndrome, toxic epidermal necrolysis, viral keratoconjunctivitis and limbic keratoconjunctivitis), dermatitis (including contact dermatitis, atopic dermatitis), blepharitis (including chronic anterior blepharitis, chronic posterior blepharitis), entropion (including paralytic entropion, involutional entropion), floppy eyelid syndrome, thyroid ophthalmopathy, pterygium, conjunctivochalasis, epithelial damage induced by preservatives, epithelial or anterior chamber damage induced by ocular surgery, limbal cell deficiency, corneal ulcers induced by physical or chemical agents, keratitis (including Stromal necrotic keratitis, Cogan's syndrome, Mooren's ulcer, neurotrophic keratitis, exposure keratitis, crystalline infectious keratitis, Thygeson's superficial punctate keratitis, filamentary keratitis, recurring corneal epithelial erosions, epithelial dystrophies and Meesmann's dystrophy), episcleritis and uveitis.

What is claimed is:

1. Sterile ophthalmic composition comprising:
   a) an oily phase comprising castor oil and a medium chain triglyceride,
   b) one or more surfactants wherein the resulting hydrophilic-lipophilic balance value of said one or more surfactants is from 10 to 16, and
   c) an aqueous phase wherein the composition has a pH from 5.0 to 9.0,
   wherein the castor oil and medium chain triglyceride are the sole active pharmaceutical ingredients;
   wherein the one or more surfactant is selected from the group consisting of polyoxyl castor oil with 30 to 40 oxyethylene units, polyoxyl hydrogenated castor oil with 40 to 60 oxyethylene units, sorbitan trioleate, sorbitan tristearate, sorbitan sesquioleate, sorbitan oleate, sorbitan stearate, sorbitan isostearate, sorbitan palmitate, sorbitan laurate, polyethylene glycol hexadecyl ether, glyceryl stearate, glyceryl monooleate, glycol stearate, glycol distearate, polyoxyl steraryl ether with 2 oxyethylene units, polyoxyl castor oil with 2 to 20 oxyethylene units, cetostearyl alcohol, stearyl alcohol, and mixtures thereof; and
   wherein the composition is in the form of a nanoemulsion.

2. Composition according to claim 1, wherein the castor oil and the medium chain triglyceride are in a ratio by weight of from 50:1 to 1:50.

3. Composition according to claim 1, wherein the total amount of castor oil and medium chain triglyceride is from 0.05 to 70 wt % with respect to the total weight of the composition.

4. Composition according to claim 1, wherein the medium chain triglyceride is caprylic/capric acid triglyceride.

5. Composition according to claim 1, further comprising one or more oils other than the castor oil and the medium chain triglyceride.

6. Composition according to claim 1, wherein the total amount of surfactant is from 0.1 to 40 wt % with respect to the total weight of the composition.

7. Composition according to claim 1, further comprising one or more tonicity adjusting agents.

8. Composition according to claim 1, further comprising one or more pH adjusting agents.

9. Composition according to claim 1, further comprising from 0.1 to 10 wt % of one or more viscosity increasing agent selected form the group consisting of sodium alginate, polyvinylpyrrolidone, gellan gum, chitosan, and mixtures thereof, with respect to the total weight of the composition.

10. Composition according to claim 1, wherein the composition comprises at least 80 wt % of water with respect to the total weight of the composition.

11. Composition according to claim 1, further comprising one or more viscosity increasing agent selected from the group consisting of polyvinylpirrolidones; polyvinyl alcohol; xanthan gum; guar gum; welan gum; gellan gum; tragacanth gum; ceratonia gum; agar; methylcellulose; ethylcellulose; hydroxyethyl cellulose; hydroxyethylmethyl cellulose; hydroxypropyl cellulose; hydroxypropylmethyl cellulose; hydroxypropylmethyl cellulose phthalate; hydroxypropylmethyl cellulose acetate succinate; sodium carboxymethylcellulose; calcium carboxymethylcellulose; polyethylene glycol; glycerine; carrageenan; alginic acid; sodium alginate; potassium alginate; propylene glycol alginate; hyaluronic acid; sodium hyaluronate; carbomer; polycarbol; poloxamers; chitosan; maltodextrin; and mixtures thereof.

12. A method for the treatment of an ocular disease selected from the group consisting of dry eye, keratoconjunctivitis sicca, xerophthalmia, xerosis, Sjogren's syndrome, conjunctivitis, allergic conjunctivitis, vernal keratoconjunctivitis, atopic keratoconjunctivitis, pemphigoid, Stevens-Johnson syndrome, toxic epidermal necrolysis, viral keratoconjunctivitis, limbic keratoconjunctivitis, contact dermatitis, atopic dermatitis, anterior blepharitis, chronic posterior blepharitis, entropion, floppy eyelid syndrome, thyroid ophthalmopathy, pterygium, conjunctivochalasis, epithelial damage induced by preservatives, epithelial or anterior chamber damage induced by ocular surgery, limbal cell deficiency, conical ulcers induced by physical or chemical agents, keratitis, Cogan's syndrome, Mooren's ulcer, recurring corneal epithelial erosions, epithelial dystrophies and Meesmann's dystrophy, episcleritis and uveitis by administering to a subject in need thereof an effective amount of a sterile ophthalmic composition according to claim 1.

* * * * *

UNITED STATES PATENT AND TRADEMARK OFFICE
CERTIFICATE OF CORRECTION

PATENT NO. : 10,660,848 B2
APPLICATION NO. : 15/644286
DATED : May 26, 2020
INVENTOR(S) : Izquierdo Torres et al.

Page 1 of 1

It is certified that error appears in the above-identified patent and that said Letters Patent is hereby corrected as shown below:

On the Title Page

Item (30) Foreign Application Priority Data, "(EP) ..........................16382321" should be
-- (EP) ..........................16382321.4 --.

Signed and Sealed this
Fourteenth Day of July, 2020

Andrei Iancu
*Director of the United States Patent and Trademark Office*